United States Patent [19]

Heinzel et al.

[11] Patent Number: 4,845,076

[45] Date of Patent: Jul. 4, 1989

[54] DNA SEQUENCES CODING FOR PROTEINS HAVING THE BIOLOGICAL ACTIVITY OF HUSI-TYPE I INHIBITORS, BIOTECHNOLOGICAL METHODS FOR THE PREPARATION OF SAID PROTEINS AND PHARMACEUTICAL COMPOSITIONS CONTAINING SAID PROTEINS

[75] Inventors: Regina Heinzel, Aachen; Heribert Appelhans, Trautheim; Hans G. Gassen, Darmstadt; Werner Machleidt, Munich; Ursula Seemüller, Freudenstadt, all of Fed. Rep. of Germany

[73] Assignee: Grünenthal GmbH, Fed. Rep. of Germany

[21] Appl. No.: 1,938

[22] Filed: Jan. 9, 1987

[30] Foreign Application Priority Data

Jan. 10, 1986 [DE] Fed. Rep. of Germany ....... 3600571

[51] Int. Cl.$^4$ .......................... A61K 37/64; C07K 7/10
[52] U.S. Cl. ...................................... 514/12; 530/324
[58] Field of Search .................... 530/350, 324; 514/12

[56] References Cited

FOREIGN PATENT DOCUMENTS 8603497 6/1986 PCT Int'l Appl. .
8603519 6/1986 PCT Int'l Appl. .

OTHER PUBLICATIONS

Seemueller et al., Chem. Abstr. vol. 105, No. 92264b (1986) (Abstr. of FEBS Lett. 199(1) 43–8, (1986).
Heinzel et al., Chem. Abstr. vol. 105, No. 204140s (1986) (Abstr. of Eur. J. Biochem 160(1) 61–7, 1986).
Egbring et al., Blood, vol. 49, No. 2 (2/1977).
Rote Liste, Editio Cantor Aulendorf/Württ (1987).
The Merck Index, 10th edition, Martha Windholz, editor, Merck & Co., Inc., p. 785 (1983).
E. C. Klasen, et al., the N-Terminal Sequence of Antileukoprotease Isolated from Bronchial Secretion, Biochemical & Biophysical Research Communications, vol. 128, No. 1, pp. 285–289, Apr. 16, 1985.
O. Wallner, et al., Characterization of an Acid-Stable Proteinase Inhibitor in Human Cervical Mucus, Hoppe-Seyler's Z. Physiol. Chem. Bd. 355, S 709–715, 1974.
H. Schiessler, et al., Acid-Stable Inhibitors of Granulocyte Neutral Proteases in Human Mucous Secretions: Biochemistry & Possible Biological Function, Neutral Proteases of Human Polymorphonuclear Leukocytes, pp. 195–207, 1978.
H. Fritz, Proteinase Inhibitors in Severe Inflammatory Processes (Septic Shock & Experimental Endotozaemia): Biochemical, Pathophysiological & Therapeutic Aspects Protein Degradation in Health & Disease, Excerpta Medica, 1980, Ciba Foundation.

*Primary Examiner*—Delbert R. Phillips
*Assistant Examiner*—Christina Chan
*Attorney, Agent, or Firm*—Wegner & Bretschneider

[57] ABSTRACT

There are described DNA sequences from the genome of mammals, in particular from the human genome, coding for proteins having the biological activity of HUSI-type I inhibitors. There are further described biotechnological methods of the preparation of proteins having the biological activity of HUSI-type I inhibitors as well as pharmaceutical compositions containing said proteins.

6 Claims, 11 Drawing Sheets

Fig. 1 Amino Acid Sequence of Tryptic Fragments of HUSI-I

```
     1                               10                    15
T1  Lys-Arg-Cys-Cys-Pro-Asp-Thr-Cys-Gly-Ile-Lys-Cys-Leu-Asp-Pro-
     16                23
    Val-Asp-Thr-Pro-Asn-Pro-Thr-Arg 1                               10                    15
T2  Lys-Pro-Gly-Lys-Cys-Pro-Val-Thr-Tyr-Gly-Gln-Cys-Leu-Met-Leu
     16           20                                29
    Asn-Pro-Pro-Asn-Phe-Cys-Glu-Met-Asp-Gly-Gln-Cys-Lys-Arg
              3'  AAG ACG CTT TAC CTG CC   5'
                   A   A   C       A
                  ├─────── RH1 ───────┤

1                          11
T3  Asp-Leu-Lys-Cys-Cys-Met-Gly-Met-Cys-Gly-Lys
          3'   ACG ACG TAC CCA TAC AC   5'
                A   A       G
                            T
                            C
              ├─────── RH2 ───────┤

1                 8
T4  Ser-Cys-Val-Ser-Pro-Val-Lys-Ala
```

Fig. 2 Restriction Map of Plasmid pRH 31
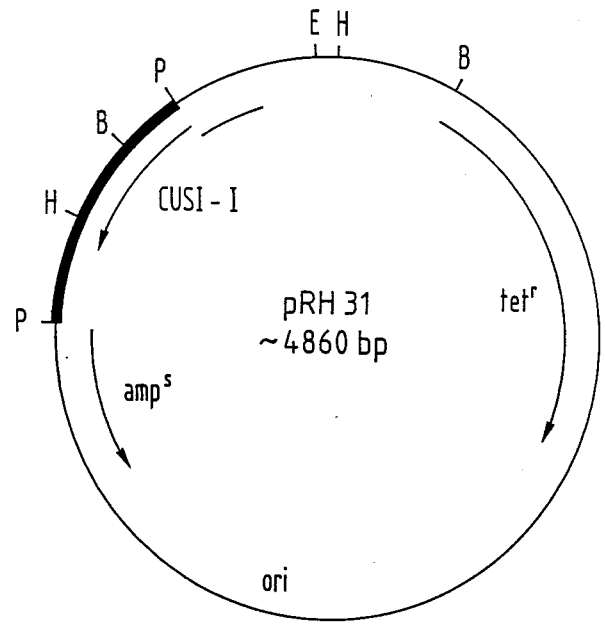
Fig. 3 Scheme of the Sequencing Strategy of the cDNA Insert of Plasmid pRH 31
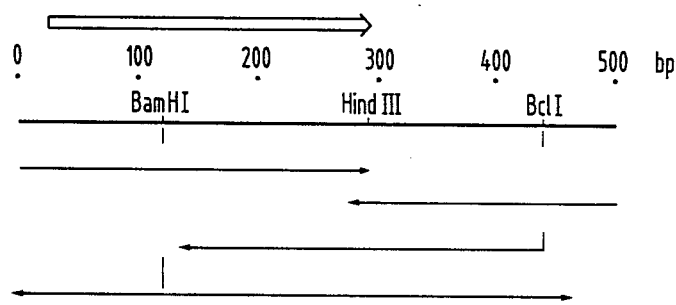

Fig. 4 Nucleotide Sequence of the CUSI-I-cDNA Fragment of Plasmid pRH 31

```
         Cys Leu Arg Tyr Lys Lys Pro
CTGCAGGGGGGGGGGGGGCCCCCCCCCACGGTGCCTTAGATACAAGAAACCT    45
GACGTCCCCCCCCCCCCCGGGGGGGGTGCCACGGAATCTATGTTCTTTGGA
                                   ——RH-5——

Glu Cys Gln Ser Asp Trp Gln Cys Pro Gly Lys Lys Arg Cys Cys
GAGTGCCAGAGTGACTGGCAGTGTCCAGGGAAGAAGAGATGTTGT           90
CTCACGGTCTCACTGACCGTCACAGGTCCCTTCTTCTCTACAACA

Pro Asp Thr Cys Gly Ile Lys Cys Leu Asp Pro Val Asp Thr Pro
CCTGACACTTGTGGCATCAAATGCCTGGATCCTGTTGACACCCCA          135
GGACTGTGAACACCGTAGTTTACGGACCTAGGACAACTGTGGGGT

Asn Pro Thr Arg Arg Lys Pro Gly Lys Cys Pro Val Thr Tyr Gly
AACCCAACAAGGAGGAAGCCTGGGAAGTGCCCAGTGACTTATGGC          180
TTGGGTTGTTCCTCCTTCGGACCCTTCACGGGTCACTGAATACCG
                                   ——RH-1——

Gln Cys Leu Met Leu Asn Pro Pro Asn Phe Cys Glu Met Asp Gly
CAATGTTTGATGCTTAACCCCCCCAATTTCTGTGAGATGGATGGC          225
GTTACAAACTACGAATTGGGGGGGTTAAAGACACTCTACCTACCG
                                        ——RH-1——

Gln Cys Lys Arg Asp Leu Lys Cys Cys Met Gly Met Cys Gly Lys
CAGTGCAAGCGTGACTTGAAGTGTTGCATGGGCATGTGTGGGAAA          270
GTCACGTTCGCACTGAACTTCACAACGTACCCGTACACACCCTTT
                      ——RH-2——
```

```
    Ser Cys Val Ser Pro Val Lys Ala Stop
    TCCTGCGTTTCCCCTGTGAAAGCTTGATTCCTGCCATATGGAG          313
    AGGACGCAAAGGGGACACTTTCGAACTAAGGACGGTATACCTC GAGGCTCTGGAGTCCTGCTCTGTGTGGTCCAGGTCCTTTCCACCC        358
    CTCCGAGACCTCAGGACGAGACACACCAGGTCCAGGAAAGGTGGG TGAGACTTGGCTTCCACCACTGATATCCTCCTTTGGGAAAGCTT         403
    ACTCTGAACCGAGGTGGTGACTATAGGAGGAAACCCTTTCCGAA GGCACACAGCAGGCTTTCAAGAAGTGCCAGTTGATCAATGAATAA        448
    CCGTGTGTCGTCCGAAAGTTCTTCACGGTCAACTAGTTACTTATT ATAAACGAGCCTATTTCTCTTTGCACCCCCCCCCCCCCCCGGGG         493
    TATTTGCTCGGATAAAGAGAAACGTGGGGGGGGGGGGGGGCCCC

TGCAG
    ACGTC
```

Fig. 5 Nucleotide Sequence of the CUSI-I-cDNA Fragment of Plasmid pRH 34

```
                                                                                               46
CTGCAGGGGGGGGGGGGGGGGGGGGGGGGGGGGGGGGGGGGGTCACT
GACGTCCCCCCCCCCCCCCCCCCCCCCCCCCCCCCCCCCCCCAGTGA

Met Lys Ser Ser Gly Leu Phe Pro Phe Leu Val                                                91
CCTGCCCTTCACCATGAAGTCCAGCGGCCTCTTCCCTTTCCTTGGTG
GGACGGGAAGTGGTACTTCAGGTCGCCGGAGAAGGGGAAGGACCAC

Leu Leu Ala Gly Thr Leu Ala Pro Trp Ala Val Glu Gly Ser                                       136
CTGCTTGCCCTAGGAACTCTGGCACTTGGGCTGTGGAAGGCTCT
GACGAACGGGATCCTTGAGACCGTGAACCCGACACCTTCCGAGA

Gly Lys Ser Phe Lys Ala Gly Val Cys Pro Pro Lys Lys Ser Ala                                   181
GGAAAGTCCTTCAAAGCTGGAGTCTGTCCTCCTAAGAAATCTGCC
CCTTTCAGGAAGTTTCGACCTCAGACAGGAGGATTCTTTAGACGG

Gln Cys Leu Arg Tyr Lys Lys Pro Glu Cys Gln Ser Asp Trp Gln                                   226
CAGTGCCTTAGATACAAGAAACCTGAGTGCCAGAGTGACTGGCAG
GTCACGGAATCTATGTTCTTTGGACTCACGGTCTCACTGACCGTC

Cys Pro Gly Lys Lys Arg Cys Cys Pro Asp Thr Cys Gly Ile Lys                                   271
TGTCCAGGGAAGAAGAGATGTTGTCCTGACACTTGTGGCATCAAA
ACAGGTCCCTTCTTCTCTACAACAGGACTGTGAACACCGTAGTTT
```

```
                                                                        Cys Leu Asp Pro Val Asp Thr Pro Asn Pro Thr Arg Arg Lys Pro
                                                                        TGCCTGGATCCTGTTGACACCCAACCCAACCCAACCAGGAGAAGCCT    316
                                                                        ACGGACCTAGGACAACTGTGGGGTTGGGTTGTTCCTCCTTCGGA

Gly Lys Cys Pro Val Thr Tyr Gly Gln Cys Leu Met Leu Asn Pro
                                                                        GGGAAGTGCCCAGTGACTTATGGCCAATGTTTGATGCTTAACCCC      361
                                                                        CCCTTCACGGGTCACTGAATACCGGTTACAAACTACGAATTGGGG

Pro Asn Phe Cys Glu Met Asp Gly Gln Cys Lys Arg Asp Leu Lys
                                                                        CCCAATTTCTGTGAGATGGATGGCCAGTGCAAGCGTGACTTGAAG      406
                                                                        GGGTTAAAGACACTCTACCTACCGGTCACGTTCGCACTGAACTTC

Cys Cys Met Gly Met Cys Gly Lys Ser Cys Val Ser Pro Val Lys
                                                                        TGTTGCATGGGCATGTGTGGGAAATCCTGCGTTTCCCCTGTGAAA      451
                                                                        ACAACGTACCCGTACACACCCTTTAGGACGCAAAGGGGACACTTT

Ala Stop
                                                                        GCTTGATTCCTGCCATATGGAGGAGGCTCTGGAGTCCTGCTCTGT      496
                                                                        CGAACTAAGGACGGTATACCTCCTCCGAGACCTCAGGACGAGACA GTGGTCCAGGTCCTTTCCACCCTGAGACTTGGCTCCACCCCCCCC      541
                                                                        CACCAGGTCCAGGAAAGGTGGGACTCTGAACCGAGGTGGGGGGGG CCCCCCCCCCCCCCCCCCTGCAG
                                                                        GGGGGGGGGGGGGGGGGGGACGTC
```

Fig. 6 Sequencing Strategy of the PstI Insert of pRH 1807
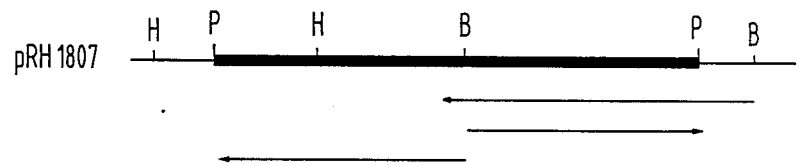
Fig. 8 Restriction Map of Plasmid pRH 34
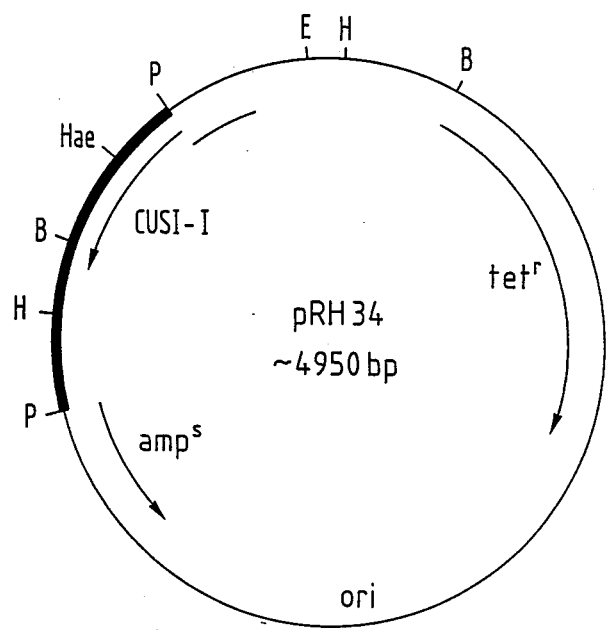

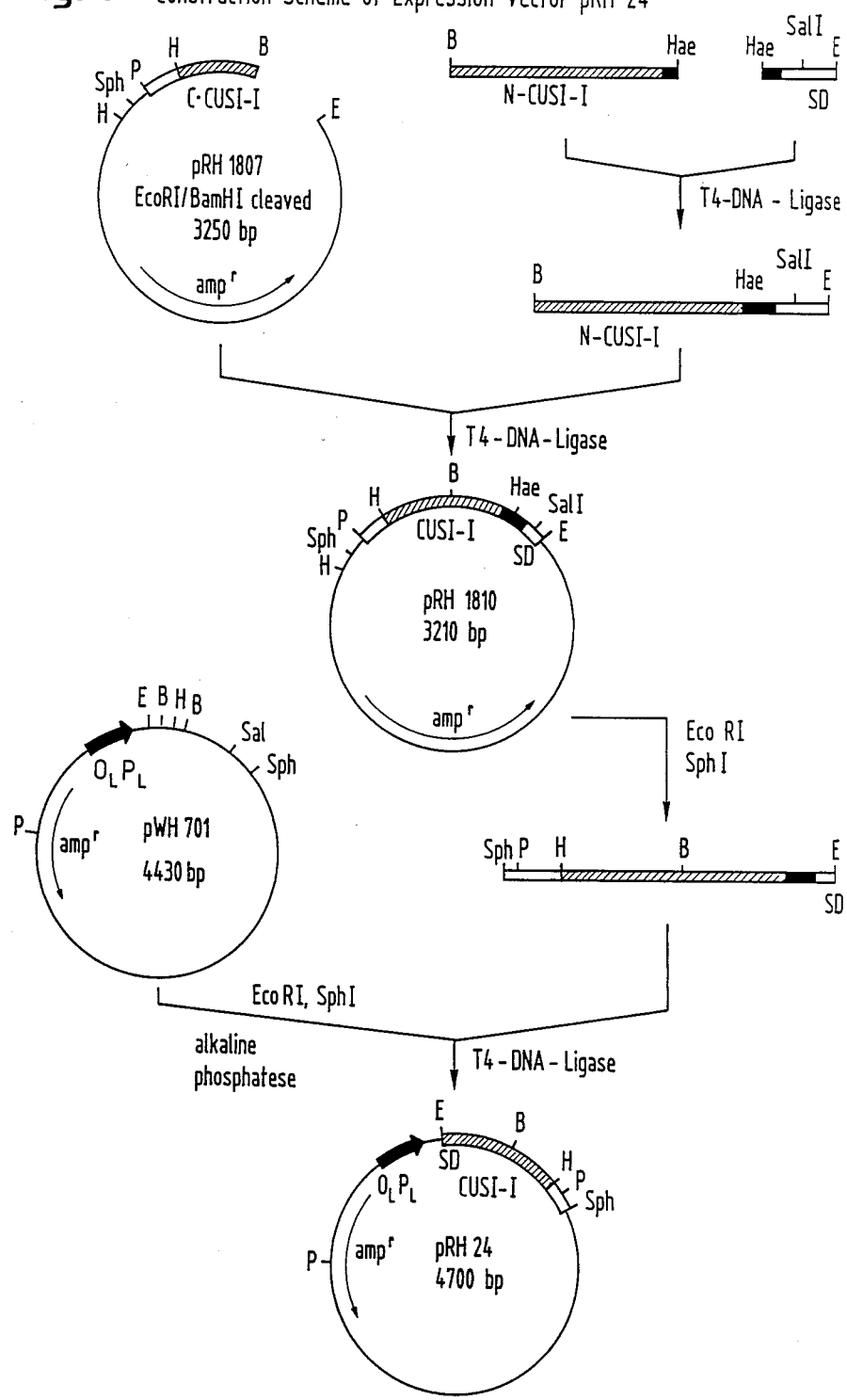
Fig. 7  Construction Scheme of Expression Vector pRH 24

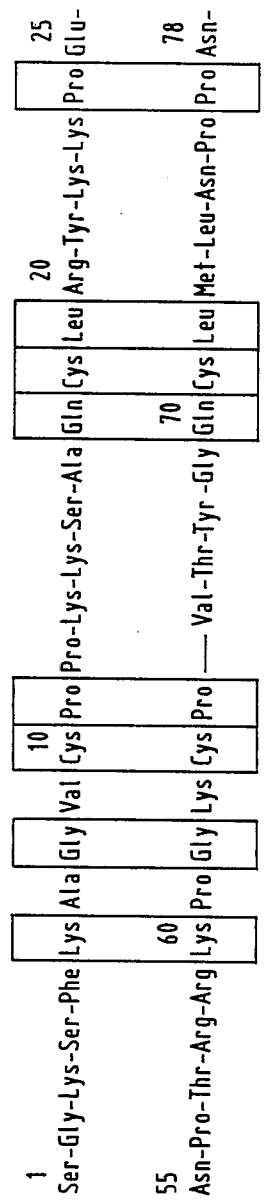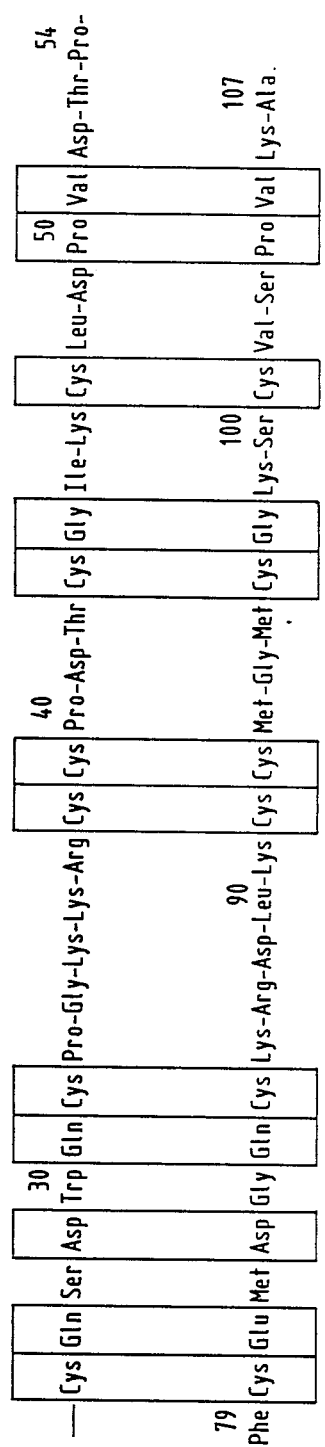
Fig. 9 Homology Approach to the Intragenic Duplication of the CUSI-I Inhibitor

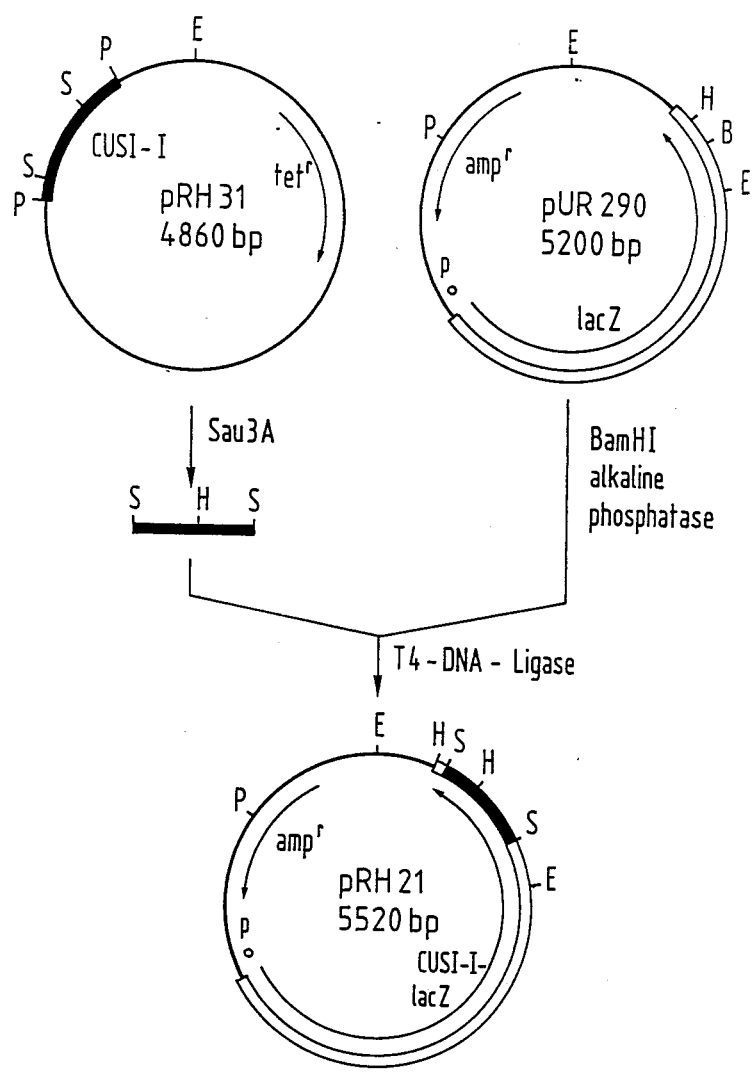
Fig. 10 Cloning Strategy for the Expression of Partial CUSI-I Sequences as β-Galactosidase Fusion Protein.

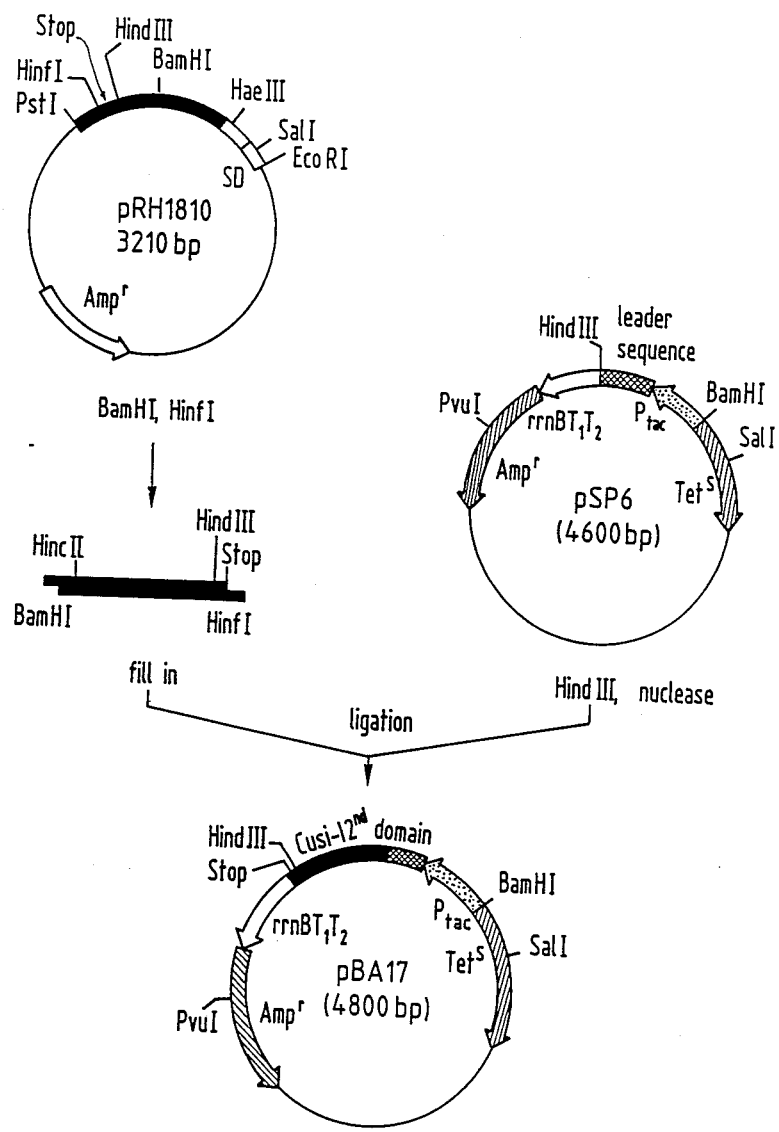
Fig. 11 Construction Scheme of Expression Plasmid pBA 17 for the Expression of the C-terminal CUSI-I Domain (= CUSI-I 2nd domain)

DNA SEQUENCES CODING FOR PROTEINS HAVING THE BIOLOGICAL ACTIVITY OF HUSI-TYPE I INHIBITORS, BIOTECHNOLOGICAL METHODS FOR THE PREPARATION OF SAID PROTEINS AND PHARMACEUTICAL COMPOSITIONS CONTAINING SAID PROTEINS

INTRODUCTION

The invention relates to DNA sequences from the genome of mammals, in particular from the human genome, coding for proteins having the biologicl activity of HUSI-type I inhibitors and to cloning and expression vectors containing such DNA sequences, using recombinant DNA technology.

The invention further relates to host organisms transformed with said vectors and to methods for the preparation of proteins having the biological activity of HUSI-type I inhibitors using said transformed host organisms.

The invention finally relates to proteins having the biological activity of HUSI-type I inhibitors and to pharmaceutical compositions containing such proteins.

BACKGROUND OF THE INVENTION

In living cells and organisms the activity of enzymes is first regulated by the novo synthesis and chemical modification of enzymes.

When fast adaptation of a cell or an organism to an altered environmental situation and simultaneously a higher activity of a specific enzyme is required, it does not mean that always a higher amount of this enzyme is synthesized de novo. Often, an already existing pool of enzymes is activated. For instance digestive enzymes (proteinases) are transferred from their storage form, the so-called zymogenes, to active proteinase. When necessary, blood coagulation factors are likewise transferred from the inactive storage form to the biologically active form.

Known activating mechanisms of storage enzymes are cleavage by specific peptidases, phosphorylation by proteinkinases, release from vesicles and the changing of the protein conformation by allosteric ligands.

An excess of activating reactions mentioned and the long-term effect of the activated enzymes is prevented by the controlled degradation or the specific inhibition of these enzymes. For example, the biological activity of activated proteinases is often blocked by specific proteinase inhibitors.

In the past few years the clinical and pathogenetic relevance of different proteinase inhibitors was recognized (1,2). It was found that lysosomal proteinase inhibitors are suitable for the therapy of sepsis, of chronic diseases of the rheumatic type as well as of diseases of the upper pulmonary system. At the moment, however, there are not proteinase inhibitors known that could be used in the treatment of these diseases. For the time being only the proteinase inhibitor aprotinin is used in therapy. Aprotinin is used for the treatment of postoperative haemorrhages caused by hyperfibrinolysis and the early treatment of shocks.

For the therapy of the above-mentioned diseases HUSI (Human-Seminalplasma Inhibitor)-type I inhibitors might be suitable. They are proteins. Examples for the group of HUSI-type I inhibitors are the proteinase inhibitors HUSI-I, CUSI-I (Cervix-Uterus-Secretion Inhibitor) and BSI (Bronchial-Secretion Inhibitor).

HUSI-I is an acid-resistant proteinase inhibitor from human seminal plasma and inhibitors proteinases from the lysosomal granula of the granulozytes, such as elastase. HUSI-I only exhibits a reduced inhibitory activity against other intracellular or extracellular proteinases. Its molecular weight is about 11,000. A partial amino acid sequence of HUSI-I was published by Fritz (48).

In addition to HUSI-I there exists a further acid-resistant proteinase inhibitor in the human seminal plasma, namely HUSI-II (3). Its molecular weight is about 6,500. HUSI-I and HUSI-II have completely different inhibitory spectra. While the inhibitory activity of HUSI-II is limited to trypsin and akrosin, the most remarkable property of HUSI-I is the specific inactivation of proteases from the lysosomal granula of the granulozytes, e.g. of elastase. Because of its different biological activity, HUSI-II is thus no HUSI-I inhibitor.

The acid-resistant inhibitor CUSI-I was isolated from the cervix-uterus secretion (4). The molecular weight of CUSI-I is almost identical with that of HUSI-I. Moreover, HUSI-I and CUSI-I have the same inhibition spectrum. In the Ouchterlony immuno-diffusion test HUSI-I and CUSI-I show immunological cross-reaction with anti-HUSI-I antibodies (5, 6). Finally, the amino acid analyses of HUSI-I and CUSI-I, so far only fragmentarily known, are almost identical (47).

The bronchial-secretion inhibitor (BSI) was isolated from the bronchial secretion (41, 44, 45, 46). The sequence of the first 25 amino acids of BSI was incompletely published in (41). BSI has a molecular weight of about 10,000. In immunological tests BSI shows a cross-reaction with rabbit anti-HUSI-I antibodies (47). BSI is acid-resistant and inhibits the proteinases leukozyte elastase, cathepsin G, trypsin and chymotrypsin.

Although the biological activity of HUSI-type I inhibitors was essentially known, so far these inhibitors could not be used for therapeutical purposes since they were not available in sufficient amounts in essentially pure form.

SUMMARY OF THE INVENTION

Thus the problem underlying the present invention is to provide DNA sequences coding for proteins with the biological activity of HUSI-type I inhibitors and to prepare by biotechnological methods proteins with the biological activity of HUSI-type I inhibitors using such DNA sequences.

This problem is solved by providing DNA sequences derived from a mammalian genome, particularly from the human genome, which hybridize, preferably under stringent conditions, to a DNA sequence according to FIG. 4 and/or 5 and which code for proteins having the biological activity of HUSI-type I inhibitors.

In the present invention, the expression "proteins having the biological activity of HUSI-type I inhibitors" relates to fusion proteins and non-fusion proteins having the biological activity of the inhibitors HUSI-I, CUSI-I or BSI, i.e. for example the immunological properties of the natural proteins and/or the specific inhibitory properties of natural proteins. The inhibitory activity of the proteins of the invention having the biological activity of HUSI-type I inhibitors is in the following determined by measuring the inhibition of the enzyme chymotrypsin. As regards the expression "hybridizing under stringent conditions" and "conventional hybridization conditions" see (28), pages 387-389, and Bonner et al. (28). In general Tm -15 to Tm -30, preferably Tm -20 to Tm -27 is used. Fusion proteins and also non-fusion proteins, which embrace only part of the amino acid sequences of HUSI-I, CUSI-I and BSI are called in the invention proteins having the biological activity of HUSI-type I inhibitors. Partial regions of the amino acid sequence of proteins are also called "domains".

In a preferred embodiment of the present invention, the DNA sequences code for proteins having the biological activity of the CUSI-I protein. In a further preferred embodiment of the present invention, the DNA sequence codes for a protein having the amino acid sequence shown in FIG. 5.

Particularly preferred embodiments of the present invention are the DNA sequences shown in FIGS. 4 and 5 which are contained in plasmids pRH31 and pRH34 in the form of PstI fragments. Plasmids pRH31 and pRH34 have been deposited with the Deutsche Sammlung für Mikroorganismen (DSM) under deposition Nos. DSM 3634 and DSM 3635, respectively. Plasmids pRH31 and pRH34 or fragments and synthetic oligonucleotides derived thereof are suitable as probes for the identification and isolation of further DNA sequences which code for proteins having the biological activity of the HUSI-type I inhibitors, i.e. for example for HUSI-I and BSI. This conclusion is possible for the expert since the primary structure data of inhibitors HUSI-I and BSI, although incomplete, which are available so far, show great similarity. From this a high sequence homology on DNA level can be expected. Because of this high sequence homology, it cannot be excluded that only a single gene codes for all three inhibitors and that the individual inhibitors are tissue-specific expression products.

Suitable for the purposes of the present invention are also DNA sequences hybridizing, preferably under stringent conditions, to one of the above DNA sequences. Said DNA sequences are either of natural, semisynthetic or synthetic origin, they are related to one of the above-mentioned DNA sequences by mutations, nucleotide substitutions, nucleotide deletions, nucleotide insertions or inversion of nucleotide regions and they code for proteins with the biological activity of HUSI-type I inhibitors.

Subject matter of the invention are furthermore vectors for the cloning and expression of the above-mentioned DNA sequences. In the invention, the term "vectors" relates e.g. to plasmids, such as pBR322, pU18, pUR290, pWH701 and pSP6 or to virus genomes and their fragments or derivatives, e.g. to the genome of the lambda phage or of the phage M13. In expression vectors of the present invention, the inventive DNA sequence is operatively linked to an expression control sequence.

In a preferred embodiment, the expression vector at the 5' end of the gene contains a DNA fragment having the following sequence:

```
5' A A T T C G G A G G T G T C G A C T A T G A A G T C C A G C G G 3'
       G C C T C C A C A G C T G A T A C T T C A G G T C G C C
```

As expression control sequences (promoter systems) according to the invention there may be used the E. coli lac promoter, the E. coli trp promoter, the E. coli lipoprotein promoter, the alkaline phosphatase promoter, the lambda-$P_L$ promoter, the lambda $P_R$ promoter, a yeast expression control sequence or other eukaryotic expression control sequences.

Particularly preferred plasmids of the present invention are plasmids pRH31 (DSM 3634) and pRH34 (DSM 3635). Further particularly preferred plasmids are plasmids pRH24, pRH21 and pBA17 which may be constructed with plasmids pRH31, pRH34 and pRH1810 (DSM 3905).

A further subject matter of the invention are host organisms which have been transformed with the above-mentioned vectors. Preferred host organisms are strains of the species E. coli, Bacillus subtilis or other bacteria, Saccharomyces cerevisiae, other microscopically small fungi, animal or human cells.

Subject matter of the present invention are furthermore proteins having the biological activity of HUSI-type I inhibitors. The proteins of the invention preferably exhibit the biological activity of the CUSI-I protein.

In a particularly preferred embodiment, the protein having the biological activity of the CUSI-I protein exhibits the amino acid sequence shown in FIG. 5.

In a further particularly preferred embodiment, the protein having the biological activity of the CUSI-I protein has the following amino acid sequence Pro-Val-Asp-Thr-Pro-Asn-Pro-Thr-Arg-Arg-Lys-
Pro-Gly-Lys-Cys-Pro-Val-Thr-Tyr-Gly-Gln-Cys-
Leu-Met-Leu-Asn-Pro-Pro-Asn-Phe-Cys-Glu-
Met-Asp-Gly-Gln-Cys-Lys-Arg-Asp-Leu-Lys-
Cys-Cys-Met-Gly-Met-Cys-Gly-Lys-Ser-Cys-Val-
Ser-Pro-Val-Lys-Ala-OH.

In a further particularly preferred embodiment, the protein having the biological activity of the CUSI-I protein has the following amino acid sequence Asp-Pro-Val-Asp-Thr-Pro-Asn-Pro-Thr-Arg-Arg-
Lys-Pro-Gly-Lys-Cys-Pro-Val-Thr-Tyr-Gly-Gln-
Cys-Leu-Met-Leu-Asn-Pro-Pro-Asn-Phe-Cys-
Glu-Met-Asp-Gly-Gln-Cys-Lys-Arg-Asp-Leu-
Lys-Cys-Cys-Met-Gly-Met-Cys-Gly-Lys-Ser-
Cys-Val-Ser-Pro-Val-Lys-Ala-OH.

The proteins of the invention are preferably essentially pure proteins.

The invention further relates to a process for the preparation of the above-mentioned proteins comprising culturing one of the above-mentioned transformed host organisms in a conventional nutrient medium, optionally including the expression of the gene product, isolating the expression product from the culture, i.e. fro the cultivated cells and/or from the nutrient medium and optionally further treating the expression product under controlled acidic hydrolytic conditons to effect a partial hydrolysis and separating the desired biologically active protein fragment from the hydrolysate by gel chromatography. Depending on their use, the proteins thus obtained can be further purified, preferably by chromatography, e.g. affinity chromatography or high performance liquid chromatography (HPLC) or a combination of these methods.

The proteins and protein fragments prepared according to the invention are particularly suitable for the treatment of chronic bronchitis, of chronic cervix inflammations, as well as for the treatment of other chronic inflammatory processes associated with excessive mucous secretion and acute emergency situations resulting therefrom. They are further suitable for the early treatment of shocks and e.g. for the treatment of postoperative haemorrhages due to hyperfibrinolysis. Correspondingly, pharmaceutical compositions comprising an effective amount of a protein having the biological activity of the HUSI-type I inhibitors and conventional carriers and/or diluents and/or adjuvants are also a subject matter of the present invention.

For treatment, the protein having the biological activity of HUSI-type I inhibitors may be administered in the form of sterile isotonic solutions by intramuscular, intravenous or subcutan injections into the inflammed area or optionally by infusion. In the invention, pharmaceutical compositions in the form of sprays or inhalation preparations are preferred. They are particularly suitable for the treatment of diseases of the respiratory tract by direct application of the active ingredients to the affected parts of the bronchial tubes and te lungs.

In a first aspect of the present invention there is provided a composition comprising an acid-resistant proteinase inhibitor HUSI-type I protein in a form essentially free from impurities which interfere with activity of said protein as an antiinflammatory agent; and any additional ingredients being biologically inert to said activity.

In a preferred embodiment of this aspect provides an acid resistant proteinase inhibitor HUSI-type I protein having an amino acid sequence including at least that portion capable of imparting said HUSI-type I activity from the amino acid sequence of the formula:

Pro-Val-Asp-Thr-Pro-Asn-Pro-Thr-Arg-Arg-Lys-
Pro-Gly-Lys-Cys-Pro-Val-Thr-Tyr-Gly-Gln-Cys-
Leu-Met-Leu-Asn-Pro-Pro-Asn-Phe-Cys-Glu-
Met-Asp-Gly-Gln-Cys-Lys-Arg-Asp-Leu-Lys-
Cys-Cys-Met-Gly-Met-Cys-Gly-Lys-Ser-Cys-Val-
Ser-Pro-Val-Lys-Ala-OH.

In another preferred embodiment of this aspect provides an acid resistant proteinase inhibitor HUSI-type I protein having an amino acid sequence including at least that portion capable of imparting said HUSI-type I activity from the amino acid sequence of the formula:

Asp-Pro-Val-Asp-Thr-Pro-Asn-Pro-Thr-Arg-Arg-
Lys-Pro-Gly-Lys-Cys-Pro-Val-Thr-Tyr-Gly-Gln-
Cys-Leu-Met-Leu-Asn-Pro-Pro-Asn-Phe-Cys-
Glu-Met-Asp-Gly-Gln-Cys-Lys-Arg-Asp-Leu-
Lys-Cys-Cys-Met-Gly-Met-Cys-Gly-Lys-Ser-
Cys-Val-Ser-Pro-Val-Lys-Ala-OH.

The terminology "a form essentially free from impurities which interfere with activity of said protein" refers to the exclusion from the scope of the present invention of any impurities stemming from the isolation process of the protein which interfere with the antiinflammatory activity of the protein. Also, the "additional ingredients" encompass conventional additives and excipients which also do not interfere with the antiinflammatory activity of the protein.

A second aspect of the present invention provides an acid-resistant proteinase inhibitor HUSI-type I protein having an amino acid sequence transcribed from DNA having a sequence capable of imparting said HUSI-type I activity, said amino acid sequence including at least that portion of FIG. 5 capable of imparting said HUSI-type I activity.

A third aspect of the present invention provides a method of treating a patient suffering from a chronic inflammatory disease or postoperative hemorrhages which comprises administration to said patient of an effective amount of an acid-resistant proteinase inhibitor HUSI-type I protein having an amino acid sequence transcribed from DNA having a sequence capable of imparting said HUSI-type I activity, said sequence including at least that portion of FIG. 5 capable of imparting said HUSI-type I activity.

A preferred embodiment of this aspect involves the administration of the acid-resistant proteinase inhibitor HUSI-type I protein through inhalation.

A further aspect of the present invention provides a composition comprising an acid-resistant proteinase inhibitor CUSI-type I protein in a form essentially free from impurities which interfere with activity of said protein as an antiinflammatory agent; and any additional ingredients being biologically inert to said activity.

In a preferred embodiment of this aspect provides an acid resistant proteinase inhibitor CUSI-type I protein having an amino acid sequence including at least that portion capable of imparting said CUSI-type I activity from the amino acid sequence of the formula:

Pro-Val-Asp-Thr-Pro-Asn-Pro-Thr-Arg-Arg-Lys-
Pro-Gly-Lys-Cys-Pro-Val-Thr-Tyr-Gly-Gln-Cys-
Leu-Met-Leu-Asn-Pro-Pro-Asn-Phe-Cys-Glu-
Met-Asp-Gly-Gln-Cys-Lys-Arg-Asp-Leu-Lys-
Cys-Cys-Met-Gly-Met-Cys-Gly-Lys-Ser-Cys-Val-
Ser-Pro-Val-Lys-Ala-OH.

In another preferred embodiment of this aspect provides an acid resistant proteinase inhibitor CUSI-type I protein having an amino acid sequence including at least that portion capable of imparting said CUSI-type I activity from the amino acid sequence of the formula:

Asp-Pro-Val-Asp-Thr-Pro-Asn-Pro-Thr-Arg-Arg-
Lys-Pro-Gly-Lys-Cys-Pro-Val-Thr-Tyr-Gly-Gln-
Cys-Leu-Met-Leu-Asn-Pro-Pro-Asn-Phe-Cys-
Glu-Met-Asp-Gly-Gln-Cys-Lys-Arg-Asp-Leu-
Lys-Cys-Cys-Met-Gly-Met-Cys-Gly-Lys-Ser-
Cys-Val-Ser-Pro-Val-Lys-Ala-OH.

In another aspect of the present invention there is provided an acid-resistant proteinase inhibitor CUSI-type I protein having an amino acid sequence transcribed from DNA having a sequence capable of imparting said CUSI-type I activity, said amino acid sequence including at least that portion of FIG. 5 capable of imparting said CUSI-type I activity.

In a final aspect of the present invention there is provided a method of treating a patient suffering from a chronic inflammatory disease or postoperative hemorrhages which comprises administration to said patient of an effective amount of an acid-resistant proteinase inhibitor CUSI-type I protein having an amino acid sequence transcribed from DNA having a sequence capable of imparting said CUSI-type I activity, said sequence including at least that portion of FIG. 5 capable of imparting said CUSI-type I activity.

A preferred embodiment of this aspect involves the administration of the acid-resistant proteinase inhibitor CUSI-type I protein through inhalation.

DESCRIPTION OF THE INVENTION

In order to construct a host organism which is able to synthesize a foreign protein it is necessary to carry out a number of experimental steps. First the gene carrying the information for the biosynthesis of the desired protein is identified and isolated. There are different methods known for the identification and isolation of genes.

For example, for isolating a DNA sequence coding for a protein with the biological activity of the CUSI-I protein, there are first prepared two mixtures of synthetic oligonucleotides on the basis of partial protein sequence data of the HUSI-I protein. These oligonucleotides are complementary to a DNA sequence encoding 6 amino acids and can be used as gene probes (cf. FIG. 1, RHI and RH2).

On the basis of the incomplete data on the primary structure of CUSI-I, HUSI-I (48) and BSI (41), it was not possible to synthesize suitable oligonucleotide mixtures. For the known data of the amino acid sequences were obtained on the basis of chemically non-uniform mixtures of tryptic fragments, of bromocyano fragments or of $NH_2$-termini (48). The partial sequences thus obtained moreover deviate by more than 30% from the amino acid sequence of the CUSI-I protein determined according to the invention. It is well-established that already one single incorrectly determined amino acid in a sequence of amino acids can lead to the inoperability of the oligonucleotide probe derived from this amino acid sequence.

In (48) for example the amino acid sequence in the region of RH2 is stated to be Cys-Ser-Met-Gly-Met-Cys, the amino acid sequence determined according to the invention in this region is, however, Cys-Cys-Met-Gly-Met-Cys (see FIG. 4).

According to the invention, cDNA libraries are screened using the above-mentioned mixtures of synthetic oligonucleotides. These cDNA libraries were prepared with mRNA from human cervix tissue as starting material. As starting material for the preparation of a cDNA library according to the present invention there may also be used mRNA from the tissue of the upper respiratory tract of the human lung (autopsy material, taken 10 hours post mortem) (7). The mRNA isolated from the donor tissue is used in a conventional manner for the synthesis of complementary DNA (cDNA) molecules, which are finally inserted into the PstI site of plasmid pBR322. With the thus prepared cDNA molecules host organisms, e.g. E. coli K12 DH1, are transformed and in a conventional manner plated on agar plates containing tetracycline.

Colonies of transformed host bacteria containing a plasmid with a cDNA sequence coding for a protein with the biological activity of the CUSI-I protein are identified in a hybridization experiment, the so-called colony hybridization. For this experiment a replica nitrocellulose filter is prepared from bacteria colonies growing on agar plate, cf. Thayer (8). The replica nitrocellulose filters are then hybridized with the two above-mentioned oligonucleotide mixtures according to Wallace (9). From the positive colonies, the recombinant cDNA-containing plasmid is isolated. The size of the cDNA insert in the plasmid is determined and a plasmid with an insert of appropriate size is characterized in more detail by an analysis of the DNA sequence of the cDNA insert. Thus the recombinant plasmid pRH31 is isolated. It is deposited with the Deutsche Sammlung für Mikroorganismen under deposition no. DSM 3634.

By further screening a cDNA library prepared from nRNA of cervix tissue samples with an oligonucleotide derived from the DNA sequence of plasmid pRH31 and acting as probe in the hybridization the recombinant plasmid pRH34 is isolated (see FIG. 4, RH5). When determining the DNA sequence of the insert of recombinant plasmid pRH34 it can be seen that this plasmid comprises the whole region coding for the CUSI-I protein. Recombinant plasmid pRH34 has been deposited with the Deutsche Sammlung für Mikroorganismen under deposition no. DSM 3635.

With the assistance of the cDNA sequences contained in plasmids pRH31 and pRH34 expression vectors are then constructed. First recombinant plasmid pRH24 is prepared from recombinant plamid pRH1810 acting as intermediate. Recombinant expression plasmid pRH24 contains the region of plasmid pRH34 coding for a protein with the biological activity of the CUSI-I protein as well as a synthetized DNA fragment comprising both the Shine-Dalgarno sequence and the translation origin. The expression product derived from recombinant expression vector pRH24 comprises all amino acids shown in FIG. 5.

Furthermore recombinant expression plasmid pRH21 is prepared. For this a SauIIIA fragment is cut out from plasmid pRH31 and inserted into the BamHI restriction site of plasmid pUR290. The expression product derived from the thus constructed recombinant expression plasmid pRH21 is a fusion protein whose N-terminus consists of the amino acid sequence of the β-galactosidase and whose 59 C-terminal amino acids correspond to the last 59 amino acids of the CUSI-I protein (see FIG. 5). A polypeptide having a length of 58 amino acids is separated in a conventional manner from this expression product by acidic hydrolysis of the aspartic acid-proline linkage (e.g. by treating for 20 to 40 hours with 10 to 70% acetic acid or formic acid, preferably with about 30% acetic acid or 70% formic acid, at temperatures in the range from about 10° to 30° C., preferably at room temperature). It is subsequently purified by gel chromatography. This polypeptide having a length of 58 amino acids corresponds to the C-terminal domain of the protein described in FIG. 5 having the biological activity of the CUSI-I protein.

Plasmid pBA17 is constructed as a further recombinant expression plasmid. For this a BamHI/HinfI fragment is cut out from plasmid pRH1810 and ligated into expression plasmid pSP6 after the ends have been filled up. The expression plasmid is prepared for ligation by HindIII cleavage and subsequent treatment with Mungbean nuclease and alkaline phosphatase. The expression product obtained from the resulting recombinant expression plasmid pBA17 consists of 59 amino acids. Its sequence corresponds to the one of the 59 C-terminal amino acids in FIG. 5. The expression product exhibits the biological activity of the CUSI-I protein.

The expression of the above-mentioned proteins by the corresponding transformed host organisms is demonstrated by an immunoprecipitation (10) or by a Western blot analysis (11, 12). The biological activity of the expression products is determined by the inhibition of the proteinase chymotrypsin.

The Figures show:

FIG. 1: Amino acid sequence of fragments of the natural HUSI-I protein which were purified by HPLC and obtained by enzymatic cleavage of the protein with trypsin. The sequence regions from which the two mixtures of synthetic oligonucleotides were derived are called RH1 and RH2. They are underlined.

FIG. 2: Restriction map of plasmid pRH31. Recombinant plasmid pRH31 is shown with restriction sites of P=PstI, E=EcoRI, B=BamHI, H=HindIII.

The black bar shows the cDNA insert, the arrows in the circle show the tetracycline-resistance gene (tet$^r$) and the interrupted ampicillin-resistance gene (amp$^s$).

FIG. 3: Scheme of the sequencing strategy of the cDNA insert of plasmid pRH31. The black bar shows the 500 bp-Pst I fragment of plasmid pRH31, the black arrows correspond in each case to a sequencing reaction. The white, unfilled arrow designates the region on the cDNA insert coding for CUSI-I.

FIG. 4: Nucleotide sequence of the CUSI-I-cDNA fragment of plasmid pRH31. The double-stranded DNA sequence is shown. The open reading frame of the CUSI-I sequence starts immediately after the 5'-(G:C). homopolymer tail of the cDNA insert. The reading frame encodes 90 amino acids which are indicated in the three letter code. Further shown are 178 base pairs following the stop codon TGA.

FIG. 5: Nucleotide sequence of the CUSI-I-cDNA fragment of plasmid pRH34. The double-stranded DNA sequence is shown. The amino acids derived from the DNA sequence are given in the three letter code. The nucleotides from position 59 to 133 encode the signal peptide of the CUSI-I protein.

FIG. 6: Sequencing strategy of the PstI insert of pRH1807 (containing the CUSI-I cDNA fragment of the plasmid pRH34). Each arrow represents a sequencing experiment. H=HindIII, P=PstI, B=BamHI.

FIG. 7: Construction scheme of expression vector pRH24 which carries the CUSI-I gene at the 3'-end of the regulatable promoter lambda-P$_L$.

| amp$^r$: | ampicillin-resistance gene |
|---|---|
| N-CUSI-I: | DNA fragment coding for the CUSI-I-N terminus |
| C-CUSI-I: | DNA fragment coding for the CUSI-I-C terminus |
| O$_L$P$_L$: | Left operator and promoter region of the bacteriophage lambda |
| SD: | Shine-Dalgarno sequence or ribosome-binding site |

Abbreviations of the restriction endonucleases: B=BamHI, E=EcoRI, H=HindIII, Hae=HaeIII, P=PstI, Sph=SphI FIG. 8: Restriction map of plasmid pRH34 Recombinant plasmid pRH34 is shown with restriction sites for P=PstI, E=EcoRI, B=BamHI, H=HindIII, Hae=HaeIII. The black bar indicates the position of the cDNA insert, the arrows in the circle indicate the position of the tetracycline-resistance gene (tet$^r$) and of the destroyed ampicillin-resistance gene (amp$^s$).

FIG. 9: An analysis of the amino acid sequence raises an interesting aspect: When neglecting two shifts of the sequence, all cystein residues existing in the molecule can be superimposed when the protein is divided into two halves and they are written over one anothr (amino acids 1–54 and 55–107). It is further noted that adjacent amino acids are often conserved relative to the cystein residues. There are two different explanations for this observation:

1. CUSI could comprise two almost identically folded inhibitor-active segments, namely one for trypsin and one for leukocyte elastase or chymotrypsin.
2. The protein was possibly formed on the level of the genetic code from an existing domain, both domains then having developed independently from each other.

FIG. 10: Cloning strategy for the expression of partial CUSI-I sequences as β-galactosidase fusion protein. The black bar represents partial CUSI-I sequences, the unfilled bar the β-galactosidase gene (lacZ), and the arrows in the circle show the position of the tetracycline-resistance gene (tet$^r$) or the ampicillin-resistance gene (amp$^r$). P=PstI, S=Sau3A, E=EcoRI, H=HindIII, B=BamHI, p=lac promoter, o=lac operator.

FIG. 11: Construction Scheme of Expression Vector pBA17 for the expression of the C-terminal CUSI-I domain (=CUSI-I 2nd domain). Amp$^r$=ampicillin resistance gene P$_{tac}$=tac promoter Tet$^s$=inactive tetracycline resistance residual gene rrnBT$_1$T$_2$=transcription terminator signal of ribosomal RNA genes.

The abbreviations used below have the following meanings:

| A$_{578}$ | absorption at 578 nm |
|---|---|
| DTT | dithiothreitol |
| Bis | N,N,N',N'—methylenebisacrylamide |
| bp | base pairs |
| D | Daltons |
| DE(DEAE) | diethylaminoethyl |
| ds cDNA | double-stranded cDNA |
| dNTP | deoxynucleoside-5'-triphosphate |
| EDTA | ethylenediaminetetraacetic acid |
| IgG | immunoglobulin |
| IPTG | isopropyl-β-D-thiogalactopyranoside |
| $^{32}$P | isotope of phosphorus of the relative mass 32 |
| RPM | revolutions per minute |
| $^{35}$S | sulfur isotope of relative mass 35 |
| SDS | sodiumdodecylsulfate |
| ss cDNA | single-stranded cDNA |
| TPEG | p-aminophenyl-I—thio-β-D-galactopyranoside |
| Tris | trishydroxymethylaminomethane |
| U | unit of enzyme activity |
| sarcosyl | N-laurylsarcosine |
| α-($^{32}$P)-dCTP | deoxycytidyl-5'-triphosphate with isotope $^{32}$P in the alpha phosphate residue |
| LB medium | 10 g/l casein enzymatically digested (Sigma), 5 g/l yeast extract (Sigma), 8 g/l NaCl, adjusted to pH 7.5 |

In the examples the methods described below and the mentioned materials are used. Materials and methods are further described in T. Maniatis et al. (28).

1. Enzymes

Restriction endonucleases (Bethesda Research Laboratory (BRL)) and T4-DNA ligase (Boehring Mannheim) as well as calf intestinal alkaline phosphatase (Boehringer Mannheim), T4-polynucleotidekinase (Boehringer Mannheim) and Mungbean nuclease (Pharmacia) are commercially available and used according to the manufacturer's directions. Terminal deoxynucleotidyl transferase (BRL) is used as described in section 7. E. coli DNA polymerase (BRL), ribonuclease H (BRL) as well as AMV reverse transcriptase (Life Science) are used according to (13). E. coli DNA polymerase I (Klenow fragment) (Boehringer Mannheim) is used as described in (14).

2. Microorganisms

Both gram-negative and gram-positive strains, for example strains of E. coli or Bacillus subtilis, may be used as microorganisms for the expression of a protein having the biological activity of CUSI-I.

With suitable vectors containing the structural gene for a protein having the biological activity of CUSI-I, the usual expression systems for eukaryotes, e.g. Saccharomyces cerivisiae or mammalian cells, may be used as well.

According to the invention E. coli strain K 12 MC 1061 λ 15 (deposited with DSM under deposition number DSM 3631) is used for the direct expression of the complete natural CUSI-I protein. Its genotype may be defined as follows: araD139, Δ(ara, leu) 7697, Δ lacX74, galU$^-$, galk$^-$, hsr$^-$,hsm$^+$, strA.

According to the present invention E. coli strain K12 JM 101 (deposited with American Type Culture Collection (ATCC) under deposition number ATCC 33876) is used for the expression of the fusion protein between the β-galactosidase and the C-terminal domain of the CUSI-I protein. Its genotype can be defined as follows: Δ(lac pro), thi, strA, supE, endA, sbcB, hsdR−, F'tra D36, pro AB, lacIq, ZΔM15. For isolating recombinant plasmids which were obtained after the insertion of synthetic cDNA (cf. also example 1c), E. coli K12 DH 1 (deposited with ATCC under deposition no. ATCC 33849) is used (17). Its genotype can be defined as follows: F−, recA1, endA1, gyrA96, thi-1, hsdR17 ($r_k^-$, $m_k^+$), supE44, relA1.

In order to isolate plasmids and newly constructed recombinant plasmids, containing promoter $p_L$ of the lambda-phage, E. coli K12 wild-type W6 bacteria are transformed first. In these host bacteria, the lambda-$p_L$ promoter is constantly blocked by a temperature-resistant lambda repressor, E. coli K12 wild-type W6 has been deposited with DSM under deposition number DSM 3632.

3. Vectors

For transforming E. coli bacteria, the following known plasmids are used. Some of them are commercially available.

pBR322 (ATCC 31344, (23), Pharmacia, Freiburg),
pUC18 (deposited with Deutsche Sammlung für Mikroorganismen under deposition no. DSM 3424, (24), Pharmacia, Freiburg),
pUR 290 (DSM 3417, (25)),
pWH 701 (DSM 3633, (26)),
pRK 248 cIts in E. coli K12 JMB9 (ATCC 33766, (27), (49)),
pSP6 (DSM 3904) and
pRH1810 (DSM 3905).

The man skilled in the art is familiar with further suitable vectors which may be used according to the invention in connection with host organisms that are known to him as well.

4. Gel Electrophoresis

Depending on the length of the DNA, agarose or polyacrylamide gels are used for the separation of DNA fragments. DNA fragments >800 bp are separated on 1-1.2% agarose gels in TAE buffer (40 mM Tris-acetate, pH 8.3, 2 mM EDTA), DNA fragments <800 bp on 5% polyacrylamide gels (acrylamide/bis-acrylamide (19:1) in TBE buffer (60 mM Trs-base, 60 mM boric acid, 1 mM EDTA, pH 8.3). Denaturating agarose gel electrophoresis for the separation of cDNA is for example carried out in 1.2% alkaline agarose gels according to McDonell et al. (19).

The electrophoretic separation of mRNA is carried out with 1.4% agarose gels and 15 mM methylmercurihydroxide. Samples can be subjected to electrophoresis and denaturated according to the method of Bailey et al. (20). For the separation of proteins in SDS-polyacrylamide gels, the method of Laemmli (21) is used.

5. Gel Elution Methods

The preparative separation of DNA fragments <1,000 bp is carried out in 5% polyacrylamide gels. The elution of fragments is done according to Maxam and Gilbert (22). The thus isolated fragments were used for subcloning and sequence analysis, respectively.

6. Isolation of RNA

Total RNA from human tissue is isolated according to the method of Maniatis et al. (28). The extraction of the total RNA is followed by CsCl-gradient centrifugation, in which the DNA is separated (29). For this 3 ml 5.7M CsCl, 100 mM EDTA are placed into a 16 ml Beckman-SW27 centrifuge tube, overlaid with 4 ml RNA solution (3-4 mg nucleic acid in 1% N-laurylsarcosine, 5 mM Tris-HCl, pH 7.5, 1 mM EDTA, 4 g/4 ml CsCl) and subjected to centrifugation for 17 hours at 15° C. at 17,000 rpm in a Beckman SW-27 rotor. The RNA sediment is resuspended in TE buffer (10 mM Tris-HCl, pH 8.0, 1 mM EDTA), precipitated with ethanol and finally subjected to chromatography for enrichment of poly(A+)-mRNA with oligo(dT) cellulose (Type 9, Pharamcia, Freiburg) according to Aviv and Leder (30). The mRNA is precipitated from the eluate with ethanol and kept in 70% ethanol at −70° C. The viability of the mRNA isolate can be checked by in vitro translation in rabbit reticulocyte lysate (see section 16) or by denaturating gel electrophoresis. The thus isolated mRNA is then used for cDNA synthesis and Northern blot analysis.

7. cDNA-Syhthesis

Complementary single-stranded or double-stranded DNA is synthesized according to Gubler et al. (13). The synthesis yield is screened by inserting $\alpha$-[$^{32}$P]-dCTP, while the length of the resulting cDNA-molecules is determined by 1.2% alkaline agarose gel and radioactively labelled standard DNA-molecules. Tailing of the 3'-ends of the cDNA with oligo-(dC) homopolymers is performed in a total volume of 40 μl under the following conditions: 100 mM K-cacodylate, pH 7.2, 10 mM $CoCl_2$, 1 mM DTT, 500 μM dCTP, 1-2 mg/ml cDNA, 600 U/ml terminal deoxynucleotidyl transferase. The reaction mixture is incubated for 50 minutes at 20° C. and the reaction is stopped by adding EDTA (final concentration 20 mM). After precipitation with ethanol from an 0.3 M sodium acetate solution, the precipitated cDNA is suspended in TE buffer (10 mM Tris-HCl, pH 8.0, 1 mM EDTA) and hybridized with PstI-cleaved, 3'-oligo(dG)-tailed plasmid pBR322 (100 mM NaCL, 10 mM Tris-HCl, pH 7.8, 0.1 mM EDTA, 0.1-0.3 ng/μl cDNA, 1.2 ng/μl plasmid-DNA). For hybridization this mixture is subsequently incubated for 5 minutes at 65° C., for 45 minutes at 56° C., for 45 minutes at 43° C. and for 15 minutes at room temperature. It is then directly used for transformation (see section 9).

8. Northern Blot Analysis

RNA is subjected to denaturating gel electrophoresis and transferred to nitrocellulose filters according to Thomas (31). Prehybridization and hybridization with 5'-labelled oligonucleotides can be carried out in the manner described in (9) (cf. section 11). Non-specifically bound oligonucleotides can be removed after hybridization by washing the nitrocellulose filter, e.g. by washing the filters 15 minutes at room temperature and 3 minutes at 2°·C. below the melting point in SSC buffer (900 mM NaCl, 90 mM sodium citrate, pH 7.0). The melting temperature is calculated according to Suggs et al. (32).

9. Transformation of E. coli and Isolation of Plasmids

For transformation with recombinant plasmids containing cDNA synthesized de novo (see example 1 c)), competent cells of E. coli K12 DH1 are prepared according to Hanahan (17). Cells of E. coli K12 strains JM101, W6 and Mc1061 are transformed according to Mandel and Higa (33).

Plasmid DNA is prepared from a one liter culture according to the method described in (34). Rapid analyses of plasmids are carried out according to Holmes et al. (35).

10. Oligonucleotide Synthesis

Oligonucleotides are synthesized according to the phosphoamidite method (36). Oligonucleotides are purified e.g. by reversed-phase chromatography on Shandon-Hypersil ODS® (particle size 5 μm, column size 4.6×250 mm). After removal of the trityl group with 80% acetic acid, the products are again subjected to chromatography on the mentioned column material and analysed in 20% polyacrylamide gels after labelling at the 5'-end (see section 11). According to this method two oligonucleotide mixtures, namely RH1 and RH2 are synthesized. These oligonucleotide mixtures are both used as probes. The sequences of the oligonucleotide molecules in the two mixtures are derived from appropriate amino acid sequences of tryptic fragments of the HUSI-I protein (see FIG. 1). The amino acid sequences of these fragments were determined according to W. Machleidt (50). Only by correcting known HUSI-I sequences by the analysis of several tryptic fragments and several bromocyano fragments it became possible to arrive at the oligonucleotide mixtures of the invention.

The oligonucleotide mixtures are so-called "mixed probes", i.e. mixtures of oligonucleotides differing in defined positions due to the degeneration of the genetic code (9). The disadvantages of usual "mixed probes" could be offset by high purification of the oligonucleotides with HPLC as well as by their quantitative $^{32}P$ phosphorylation. The oligonucleotide mixture RH1 corresponds to an amino acid sequence of the tryptic fragment T2 of the CUSI-I protein (see FIG. 1). Thus the oligonucleotide mixture comprises 16 different oligonucleotides, each having a length of 17 bases. The sequences are as follows:

```
3' A A G A C G C T T T A C C T G C C 5'
        A     A C         A
``` the oligonucleotide mixture RH2 corresponds to an amino acid sequence of the tryptic fragment T3 of the HUSI-I protein (see FIG. 1). There are thus synthesized 32 different oligonucleotides with a length of 17 bases each. They have the following sequences:

```
3' A C A A C A T A C C C A T A C A C 5'
       G G         G
                   C
                   T
```

11. Radioactive Labelling of DNA

The phosphorylation of chemically synthesized oligonucleotides and double-stranded dephosphorylated DNA fragments is carried out with the enzyme T4-polynucleotide-kinase in 20 to 50 μl reaction volume (50 mM Tris-HCl, pH 9.5, 20 mM MgCl$_2$, 1 mM EDTA, 10–20 pmol 5'-OH-ends substrate, 8 μl γ-[$^{32}P$]-ATP (~8000 Ci/mmol), 0.2 U/μl T4-polynucleotide-kinase), the subsequent separation of unconverted γ-[$^{32}P$]-ATP by preparative gel electrophoresis, subsequent gel elution and ion exchange chromatography on DE-52 (diaminodiethyl cellulose) (Whatman). 5'-protruding ends of DNA restriction fragments can be filled up with the Klenow fragment of the E. coli DNA polymerase I in the presence of the complementary α-[$^{32}P$]-deoxyribonucleosidetriphosphates according to Volkert et al. (14). α-[$^{32}P$]-dNTPs which are not incorporated are separated by gel permeation chromatography on Sephadex G-50 and eluted fractions are concentrated under reduced pressure.

12. DNA Sequence Analyses

The sequences of DNA molecules are determined according to Maxam and Gilbert (22).

13. Purification of the β-Galactosidase Fusion Protein

The CUSI-I-β-galactosidase fusion protein is purified by affinity chromatography according to Ullmann (37).

14. Transfer of Proteins to Nitrocellulose Filters

Proteins separated in SDS-polyacrylamide gels are transferred to nitrocellulose filters according to Towbin et al. (12).

15. CUSI-I Inhibition Tests

The activity of proteins having the biological activity of CUSI-I is shown by measuring the inhibition of trypsin (38) and chymotrysin (39).

16. Cellfree Translation of mRNA

The cellfree translation of mRNA in the reticulocyte lysate is carried out according to Pelham et al. (40) using $^{35}S$-methionin having a specific activity of 1200 Ci/mmol as radioactively labelled amino acid.

The examples illustrate the invention.

EXAMPLE 1

Cloning and Identificaton of a partial CUSI-I Protein-Specific cDNA Clone (a) Isolation and Characterization of nRNA Total RNA or mRNA is isolated from human cervix tissue (biopsy material) as described above in section 6. Approximately 1.6 to 2.2 mg total RNA are obtained from 14 to 17 g cervix tissue. After enrichment of poly(-A+)-mRNA by affinity chromatography with oligo(dT)-cellulose (Type 9, Pharmacia) 20 to 25 μg mRNA/mg total RNA are obtained. This corresponds to a yield of about 2.0 to 2.5% mRNA. An gel electrophoretic analysis in a denaturating agarose gel shows that the RNA is not degraded during isolation. Corresponding results are also obtained from an in vitro translation of the total and poly (A+)-mRNA in rabbit reticulocyte lysate.

(b) Northern blot analysis of the isolated mRNA with a synthetic oligonucleotide for detection of CUSI-I protein-specific sequences The Northern blot analysis is carried out for identifying specific mRNA sequences in the cervix-mRNA isolate. The oligonucleotide mixture RH1 which is complementary to an mRNA coding for the amino acids Phe-Cys-Glu-Met-Asp-Gly (see FIG. 1) serves as hybridizing probe. By exposure of an X-ray film ("Kodak X-o-matAR") with a nitrocellulose filter obtained during hybridization a specific signal is detected.

With the oligonucleotide mixture RH2 no positive signal was found although one of the oligonucleotide sequences of the mixture later (after sequencing) proved to be the right sequence.

When comparing the side of the molecules of the hybridizing mRNA species with DNA standard molecules in a denaturating gel it is found that the length of the hybridizing mRNA is about 650 to 800 bases.

(c) Preparation of a cDNA library with the plasmid pBR322

4 to 6 μg poly(A+)-mRNA are used as starting material for the synthesis of cDNA. The yield of single-stranded cDNA is about 280 ng (about 7%). The synthesized single-stranded c-DNA molecules have a size from about 400 to 2,500 nucleotides. From 280 ng ss cDNA about 270 ng double-stranded cDNA are obtained when synthesizing the second strand. Thus the yield of the double-strand synthesis is about 50%. The 3'-ends of the cDNA molecules are tailed with homopolymeric (dC)-regions. The thus obtained cDNA molecules are added in a hybridizing reaction to molecules of plasmid pBR322 which are PstI-cleaved and have been tailed at the 3'-ends with homopolymeric (dG)-regions. The addition products are used for the transformation of E. coli K12 DH1. Then the transformants are selected for tetracycline resistance and ampicillin sensitivity. Per ng cDNA employed, 120 transformants (12,000 transformants/100 ng ds cDNA) are obtained. The proportion of tetracycline-resistant and ampicillin-sensitive transformants or colonies is about 80%. These transformants are plated in microtiter plates (98 wells/plate) as storage cultures (medium: LB-medium, 10 g/l casein enzymatically digested (Sigma), 8 g/l NaCl, pH 7.5, 5 g/l yeast extract (Sigma), 20 μg/ml tetracycline, 20% glycerol) and kept at −20° C.

(d) Identification of a recombinant plasmid with a CUSI-I-protein-specific cDNA

For the analysis of 6,000 transformants obtained as described above, colony hybridization is carried out with the oligonucleotide mixture RH1. The activity of the oligonucleotide mixture is about $1 \times 10^6$ cpm in the hybridization volume at a specific activity of 0.8 μCi/pmol. X-ray films are exposed with the filters obtained during hybridization for 12 hours each at −70° C. in the presence of two intensifying screens. A positive signal is detected.

Starting from the storage culture of the corresponding transformant, the recombinant plasmid called pRH31 is prepred from a 0.5 liter culture (LB-medium, 10 g/l casein enzymatically digested (Sigma), 10 g/l NaCl, 5 g/l yeast extract (sigma), pH 7.5, 20 μg/ml tetracycline). By using restriction endonucleases PstI, EcoRI, BamHI as well as HindIII a restriction map of recombinant plasmid pRH31 is prepared (see FIG. 2). The cDNA insert has a length of 500 bp (see FIG. 2).

Plasmid pHR31 has been deposited with DSM under deposition number DSM 3634.

(e) Sequence analysis of the cDNA insert of pRH31

For sequencing accoding to Maxam and Gilbert (22), the PstI fragment (500 bp) from plasmid pRH31 is recloned into plasmid pUC18. For this purpose 10 μg DNA or pRH31 are cleaved with 30 U or restriction endonuclease PstI, preparatively separated on an agarose gel and the obtained 500 bp fragment is eluted from the gel. In addition 10 μg DNA of plasmid pUC18 are cleaved with restriction endonuclease PstI, dephosphorylated, extracted with phenol and diethylether and finally precipitated with ethanol from an 0.3 molar sodium acetate solution. For the following T4-DNA ligase reaction 0.2 pmol plasmid DNA and 0.4 pmol of the PstI fragment are used. The thus obtained recombinant DNA molecules are used for the transformation of E. coli K12 JM101. A selection is carried out on LB plates containing ampicillin (10 g/l casein, 8 g/l NaCl, 5 g yeast extract, 100 μg/ml ampicillin). Recombinant plasmids contained in ampicillin-resistant transformants are characterized by plasmid rapid analyses. There are obtained recombinant plasmids pRH181 and pRH182 containing the PstI fragment of pRH31 in opposite orientation. The sequencing strategy shown in FIG. 3 results from the construction of these plasmids which only serve as auxiliary constructions for easier DNA sequencing.

The nucleotide sequence of the 500 bp PstI fragment of plasmid pRH31 determined by sequencing (22) is shown in FIG. 4. The sequence starts at the 5'-end with 20 (dG)-residues. It is followed by an open reading frame extending over 273 bp (see FIG. 4, positions 25 to 297). This open reading frame codes for 90 amino acids and ends with a stop codon TGA (see FIG. 4). From the nucleotide sequence it can be seen that the oligonucleotides of the oligonucleotide mixture RH1 are complementary to positions 208 to 224 of the nucleotide sequence and that the oligonucleotides of the oligonucleotide mixture RH2 are complementary to positions 247 to 263 of the nucleotide sequence.

The stop codon TGA is followed by further 178 bp. An analysis of the nucleotide sequence demonstrates that the region coding for the N-terminal segment of the CUSI-I protein is not contained in the nucleotide sequence.

EXAMPLE 2

Isolation of a recombinant plasmid with a cDNA fragment coding for the entire CUSI-I protein (a) Synthesis of the oligonucleotide RH5

For isolating a cDNA fragment comprising the entire region coding for the CUSI-I protein, the oligonucleotide RH5 is synthesized according to the phosphamidite method (36). The oligonucleotide RH5 has a length of 20 bases. It is complementary to positions 31 to 50 of the coding DNA strand shown in FIG. 4 and has the following sequence:

The oligonucleotide RH5 is radioactively labelled and used as probe in order to identify in a new cDNA library transformants which contain recombinant plasmids, whose cDNA fragments contain at least the 5'-terminal region of plasmid pRH31 at their 5' ends.

(b) Preparation of a new cDNA gene library comprising a recombinant plasmid with the entire coding region of the CUSI-I protein.

For the preparation of a new cDNA library in E. coli using plasmid pBR322 the mRNA coding for the CUSI-I protein is isolated. For this 250 μg total RNA from human cervix tissue are electrophoretically separated according to their size in a denaturating, 1.4% "Low Melting Point" (LMP) agarose gel containing 15 nM methylmercurihydroxide (see section 4). Approximately 10 μg mRNA with a length of about 700 to 850 bases are isolated by extraction from this gel. 4 μg of this mRNA are used for cDNA synthesis (see section 7) and introduced into E. coli K12 DH1 (see section 9). There are obtained 4,300 transformants with 53 ng double-stranded cDNA. The transformants are analysed by colony hybridization with 5'-labelled oligonucleotide RH5 (see example 2a). The activity of the oligonucleotide in the hybridization solution is $2 \times 10^5$ cpm/ml with a specific activity of 0.72 μCi/pmol. There are isolated 12 transformants, the recombinant plasmid of which hybridizes with the oligonucleotide RH5. With an aliquod of the storage cultures of the transformants, the recombinant plasmids are prepared and mapped by restriction cleavages with PstI, BamHI and HindIII. It is found that 11 of these plasmids have a restriction pattern almost identical with that of plasmid pRH31, i.e. each of them contains one BamHI/PstI fragment of 380 bp and one of about 125 bp as well as one HindIII/PstI fragment of about 290 bp and one of about 200 bp. The length of the PstI fragments is in each case about 500 bp. Only one plasmid shows a different restriction map, i.e. it comprises one BamHI/PstI fragment of 285 bp and one of 275 bp as well as a HindIII/PstI fragment of about 450 bp and one of about 105 bp. The length of the insert of the deviating recombinant plasmid is about 550 bp. This recombinant plasmid is called pRH34. Its restriction map is shown in FIG. 8. Plasmid pRH34 has been deposited with DSM under deposition number DSM 3635.

(c) Nucleotide sequence of the insert of recombinant plasmid pRH34

The PstI-cDNA fragment from pRH34 and both BamHI/PstI fragments from pRH34 are subcloned in DNA of plasmid pUC18 after the DNA has been cleaved with PstI or PstI and BamHI and treated with alkaline phosphatase. The recombinant plasmids thus constructed which are auxiliary constructs for DNA sequence analysis are designated pRH1807 (PstI fragment), pRH1808 (N-terminal BamHI/PstI fragment)

EXAMPLE 3

Expression of the CUSI-I Protein in *E. coli*

(a) Construction of an expression plasmid comprising the entire CUSI-I cDNA downstream of the regulatable lambda-$p_L$ promoter.

To begin with, two synthetic oligonucleotides are synthesized which are designated RH6 and RH7. They are complementary to each other and carry the sequences for an optimal ribosome binding site (42), a SalI and EcoRI restriction site and the nucleotide sequence of the coding region of CUSI-I from position 1 to position 14. Both oligonucleotides are phosphorylated 5'-terminally with the enzyme T4-polynucleotide-kinase, preparatively electrophoretically separated in a 12% polyacrylamide gel, eluted from the gel and subjected to chromatography with DE 52. After subsequent gel permeation chromatography on Sephadex G-50 10 pmol of each oligonucleotide are mixed, denaturated at 90° C. and hybridized with each other by slow cooling to room temperature. In this way, the following double-stranded DNA fragment is obtained:

```
                                    Met  Lys  Ser  Ser
                    10              20              30
RH6 5' A A T T C G G A GG T G T C G A C T A T G A A G T C C A G C G G 3'
RH7              G C C T CC A C A G C T G A T A C T T C A G G T C G C C
      Eco RI        SD           Sal I                         HaeIII
``` and pRH1809 (C-terminal BamHI/PstI fragment). The sequence of the subcloned DNA fragments is analyzed according to Maxam and Gilbert (22). The sequencing strategy of the recombinant plasmids can be seen from FIG. 6.

The nucleotide sequence of the cDNA fragment from pRH34 is shown in FIG. 5. It is identical with the sequence of the cDNA insert of pRH31 from position 25 to 308 (see FIG. 4). However, the cDNA insert of pRH34 is 184 bp longer at the 5'-end. Of these, 143 bp correspond to the sequence complementary to the mRNA and 41 bp stem from the homopolymer tailing of the cDNA with dCTP including the PstI restriction site.

The amino acids

+4
Ser—Gly—Lys—Ser—Phe were identified as N-terminus of the HUSI-I inhibitor. When the amino acid codons are deduced from the 5'-terminal nucleotides of the isolated DNA sequence, no stop codon is found in this part of the reading frame. Thus the ATG which appears in the reading frame is responsible for the initiation and codes for the start of the CUSI-I protein. Moreover, signal peptide structures of secretory proteins are rarely longer than 25 amino acids. The restriction sites between signal peptides and the corresponding natural proteins are most often found behind the amino acids alanin, serin and glycin; thus the sequence Gly-Ser is quite common.

The primary structure of the human CUSI-I protein from cervix secretion is therefore composed of 107 amino acids. The amino acid sequence encoded by the determined nucleotide sequence is essentially identical with the N-terminal amino acid sequence of the bronchial antileukoprotease which previous to the invention was only incompletely known (41).

The second isolated component is the 210 bp (HaeIII/BamHI) fragment of plasmid pRH34 which codes for the further N-terminal region. For this, 10 μg of plasmid pRH34 are cleaved with restriction endonucleases HaeIII and BamHI and electrophoretically separated in a 5% polyamide gel. The 210 bp fragment is then eluted from the polyacrylamide gel. Plasmid pRH1807 (FIG. 6) serves as third component and thus as vector (FIG. 7). For this, 10 μg of this plasmid are cleaved with the restriction enzymes EcoRI and BamHI. The vector fragment is treated with alkaline phosphatase, then extracted with phenol and precipitated with ethanol. For the three-component ligation (FIG. 7), 1 pmol of the synthetic oligonucleotides hybridized with each other, 0.2 pmol of the N-terminal HaeIII-BamHI fragment and 0.03 pmol of the vector DNA are mixed and ligated with each other in a reaction volume of 30 μl with 5 U T4-DNA ligase. The *E. coli* K12 strain JM101 is used for transformation.

The plasmids of the transformants thus obtained are screened by hybridization with radioactively labelled oligonucleotide RH6. In addition the restriction sites for SalI, EcoRI and BamHI are checked and the length of the corresponding fragments is determined. The correct newly constructed plasmid is designated pRH1810 (DSM 3905) (FIG. 7).

For constructing an expression plasmid, 10 μg of the vector pWH701 (26) are cleaved with EcoRI and SphI, dephosphorylated, extracted with phenol and precipitated with ethanol. For preparing the EcoRI-SphI fragment from plasmid pRH1810, 10 μg DNA are cleaved with EcoRI and SphI. The resulting 525 bp fragment is separated from the vector by gel electrophoresis with a 5% polyacrylamide gel and eluted from the gel. Then 0.3 pmol vector pWH701 and 1 pmol of the EcoRI-SphI fragment are ligated with each other and introduced into *E. coli* K12 wild-type W6. The plasmids of the resulting transformants are characterized by plasmid rapid analyses and subsequent agarose gel electrophoresis. The recombinant expression plasmids are by 280 bp longer than the expression plasmids without insert. The newly identified recombinant expression plasmid is designated pRH24 and used in the subsequent expression experiments. FIG. 7 shows the construction scheme of the recombinant expression plasmid pRH24.

(b) Expression of the CUSI-I cDNA with the expression plasmid pRH24 in *E. coli* K12 MC1061/pRK248 cIts (15, 27).

The host bacteria strain alone is not lambda-lysogenic, i.e. it does not contain a lambda-cI repressor. The genetic information for the temperature-sensitive repressor lambda-cI 857 is localized on plasmid pRK248 cIts, which confers to the host bacterium also tetracycline-resistance (27). At 30° C., the lambda-$p_L$ promoter controlled transcription is completely suppressed. At 42° C., the temperature-sensitive cI 857-repressor exists in its inactivated form and the genes lying downstream of the $p_L$ promoter are transcribed.

This *E. coli* K12 MC1061/pRK248 cIts is transformed with the recombinant expression plasmid pRH24. For inducing the expression of the CUSI-I gene lying downstream of the lambda-$p_L$ promoter, 200 ml LB-medium (20 μg/ml tetracyline, 50 μg/ml ampicillin) are inoculated with 3 ml of an overnight culture of *E. coli* K12 MC1061/pRK248 cIts/pRH24 and cultured at 28° C. up to a cell density of 0.7 $A_{578}$ units/ml. Then the culture is further shaken at 42° C. In order to carry out protein analyses, before induction of the expression and at different intervals after the induction start, cell samples are taken, cells (about $1 \times 10^9$ cells) are filled up per 1 $A_{578}$ unit, centrifuged for 3 min at 12,000 g and the cell sediment is frozen at $-20°$ C. until further processing.

EXAMPLE 4

Characterization of the Crude Protein Extract after Expression of the CUSI-I Protein in *E. coli* K12 MC1061/pRK248 cIts/pRH24

(a) Test for immunological cross-reaction with rabbit-anti-HUSI-I antiserum

The cell sediments are resuspended in 60 μl disruption buffer (50 mM Tris-HCl, pH 8.0, 1 mM EDTA, 2% Triton-X-100) and 40 μl reduction buffer (4% SDS, 40% β-mercaptoethanol, 20% glycerol, 0.1% bromphenol blue) are added. The samples are subsequently incubated for 5 minutes at 100° C., then for 5 minutes in the ultrasonic bath at room temperature and again for 5 minutes at 100° C. 20 μl of the cell disruption volume are electrophoretically separated in 13.5% SDS-polyacrylamide and transferred onto nitrocellulose for an immunological assay. The nitrocellulose filter is incubated at 37° C. with "blocking" buffer (50 mM Tris-HCl, pH 7.4, 200 mM NaCl, 0.05% Tween 20, 1.5% gelatine) for 1 h in order to saturate non-specific binding sites on the filter. Rabbit-anti-HUSI-I antiserum (1:600 diluted in "blocking" buffer) is used for the first antibody reaction (incubation: 2 h at room temperature) while sheep-anti-rabbit-IgG-peroxidase conjugate is used as second antibody. The substrate reaction of the horseradish peroxidase is carried out with diaminobenzidine.

(b) Test for inhibitory activity of the proteinase inhibitor expressed in *E. coli*

Induced (6 h after start of induction) and non-induced cell samples are disrupted and tested. The cell sediments (1 $A_{578}$ unit cells) are suspended in 50 μl lysozyme disruption buffer (50 mM Tris-HCL, pH 8.0, 1 mM EDTA, 1 mg/ml lysozyme), incubated for 10 minutes at room temperature, diluted with 150 μl 50 mM Tris-HCl, pH 8.0, 1 mM EDTA, and incubated for 5 min at room temperature in the ultra sonic bath. 20 μl and 80 μl, respectively, of the crude extract of non-induced cells are tested in a chymotrysin inhibition test (39) for inhibitory activity. The results are listed in Table I.

TABLE I

Detection of the inhibitory activity of the CUSI-I protein expressed in *E. coli*

| Inhibitor test solution *E. coli* extract μl | induced | non-induced | chymotrypsin activity of 2 pmol enzyme % |
|---|---|---|---|
| — | — | — | 100 |
| 20 | — | + | 99.2 |
| 80 | — | + | 89.7 |
| 20 | + | — | 91.2 |
| 80 | + | — | 56.4 |

When comparing the activity of chymotrypsin-non-induced crude extract from *E. coli*, inhibition by cell extracts of induced cells is higher by 8 and 37%, respectively.

EXAMPLE 5

Expression of the C-terminal CUSI-I Domain as β-Galactosidase Fusion Protein in *E. coli* K12 JM101

As can be seen from FIG. 9, the structure of the CUSI inhibitor may be described as a protein molecule consisting of two domains which are formed by intragenic duplication. For expression of the C-terminal domain in *E. coli*, the DNA sequence coding for the C-terminal 59 amino acids is ligated in the correct reading frame with the DNA sequence encoding the C-terminus of the β-galactosidase of plasmid pUR290 (25). The cloning scheme is shown in FIG. 10.

10 μg of plasmid pRH31 are cleaved with restriction endonuclease Sau3A, preparatively separated in 5% polyacrylamide gel and the 320 bp CUSI-I partial fragment is eluted from the gel. pUR290 (10 μg) is cleaved with the enzyme BamHI, treated with alkaline phosphatase and ligated with the 320 bp fragment. A third of the ligated DNA is introduced into $CaCl_2$-treated *E. coli* K12 JM101 cells. The clones are selected on LB-amp agar plates (10 g/l casein enzymatically digested (Sigma), 8 g/l NaCl, 5 g/l yeast extract (Sigma), pH 7.5, 100 μg/ml, ampicillin). Since two orientations of the CUSI-I partial fragment are possible in the recombinant plasmid, plasmid rapid analyses are carried out with subsequent HindIII restriction. Clones whose plasmids contain a 165 bp HindIII fragment are further analyzed. One of these plasmids is designated as pRH21. For induction of the fusion protein expression, 100 mg LB medium containing 100 μg/ml ampicllin are inoculated with *E. coli* K12 JM101 bacteria from an overnight culture which where transformed with plasmid pRH21. The culture is incubated at 37° C. and cell growth is monitored at 578 nm. At an optical density (578 nm) of 0.5 the cultures are adjusted to 500 μmol IPTG and further incubated at 37° C. The induction of the fusion protein is followed in dependence on time and analyzed with an SDS polyacrylamide gel electrophoresis. After induction, first exclusively the CUSI-I-β-galactosidase fusion protein is formed, later also β-galactosidase. In order to show an immunological reaction with anti-CUSI-I antibodies, proteins of the *E. coli* crude extract separated electrophoretically on an SDS gel are transferred to nitrocellulose. The Western blot analysis for the specific detection of the fusion protein is carried out as described in example 4(a). The fusion protein is isolated and purified as follows:

According to (37), the IPTG analogon TPEG is bound to CH-sepharose. For purifying the CUSI-I-β-galactosidase fusion protein the strain E. coli K12 JM101 which contains the plasmid pRH21, is cultivated in 1 liter LB medium with 50 μg/ml ampicillin, and induced at a cell density of 0.5 $A_{578}$ units/ml by adjusting the medium to 0.5 mmol IPTG. After 1 h the induction phase is stopped by rapid cooling of the culture to 40° C. The cells are sedimented (5.5 g weight, moist), suspended in the lysis buffer (20 mM Tris-HCl, pH 7.4, 20 mM $MgCl_2$, 20 mM β-mercaptoethanol) and disrupted by ultrasonic treatment. The crude extract is adjusted to about 20 mg/ml protein concentrate and 1.6 mol NaCl and subjected to TPEG-Sepharose-chromatography. After washing the column material with 20 mM Tris-HCl, pH 7.4, 10 mM β-mercaptoethanol, 10 mM $MgCl_2$, 1.6M NaCl, the CUSI-I-β-galactosidase fusion protein is eluted with 100 mM sodium borate, 10 mM β-mercaptoethanol, pH 10. Chromatography was monitored by the determination of the β-galactosidase activity (43). The 1 liter culture yielded 8 mg pure CUSI-I-β-galactosidase (90%). It was further shown that the purified fusion protein also reacts with anti-HUSI-I antibodies.

For cleaving the C-terminal CUSI-I domain, the thus purified fusion protein is dissolved in 10 or 30% acetic acid or 70% formic acid. The presence of an acid-sensitive aspartic acid-proline linkage (see amino acid sequence of CUSI-I) led after a reaction time of 24–36 hours at room temperature to a 40 to 60% removal of the C-terminal CUSI-I domain. After this acid-treatment, this intact CUSI-I domain can be separated by gel filtration with G-75 and purified.

The amino acid sequence of the expressed C-terminal CUSI-I domain reads as follows:
Pro-Val-Asp-Thr-Pro-Asn-Pro-Thr-Arg-Arg-Lys-
Pro-Gly-Lys-Cys-Pro-Val-Thr-Tyr-Gly-Gln-Cys-
Leu-Met-Leu-Asn-Pro-Pro-Asn-Phe-Cys-Glu-
Met-Asp-Gly-Gln-Cys-Lys-Arg-Asp-Leu-Lys-
Cys-Cys-Met-Gly-Met-Cys-Gly-Lys-Ser-Cys-Val-
Ser-Pro-Val-Lys-Ala-OH.

This sequence is identical with positions 50–107 of the entire CUSI-I protein.

EXAMPLE 6

Expression of the C-terminal CUSI-I Domain in E. coli K12 JM101

As can be seen from example 5, the C-terminal CUSI-I domain can be expressed in E. coli K12 JM101 as β-galactosidase-fusion-protein. As shown in FIG. 11, the cDNA encoding the C-terminal 59 amino acids is linked to the signal sequence of the alkaline phosphatase gene of plasmid pSP6 in the reading frame in order to express the C-terminal CUSI-I domain as native protein. Plasmid pSP6 has been deposited with the Deutsche Sammlung für Mikroorganismen under deposition number DSM 3904. 30 μg of plasmid pRH1810 are cleaved with BamHI and HinfI. The DNA fragments are separated in 8% polyacryl amide gel. The 175 bp CUSI-I-DNA fragment coding for the C-terminal domain is eluted from the gel. The protruding DNA ends are filled up by means of the Klenow fragment of the DNA polymerase. There is obtained a 182 bp double-stranded DNA molecule with blunt ends.

3 μg of the vector pSP6 are cleaved with restriction endonuclease HindIII. The protruding single-stranded DNA ends are degraded with Mungbean nuclease and the 5'-terminal phosphate residues are removed with alkaline phosphatase.

0.3 pmol of the thus treated vector are ligated with 1 pmol of the C-terminal CUSI-I-DNA fragment. Transformation-competent (17) cells of the strain E. coli K12 DH1 are transformed with half of the obtained ligation product. The clones are selected on LB-Amp agar plates. 4 clones are identified by colony hybridization with the oligonucleotide AH12. The plasmid DNA of the clones contains DNA sequences complementary to the used probe. The oligonucleotide AH12 is complementary to the nucleotide sequence 241–258 of the CUSI-I-cDNA clone. It has the sequence

5' CCT GTT GAC ACC CCA AAC 3'.

By plasmid rapid analysis and cleavage of the DNA with HindIII and BamHI, a clone is identified containing a 540 bp DNA fragment as insert. This DNA fragment consists of the promoter region $P_{tac}$, the signal peptide sequence of the alkaline phosphatase and of the cDNA sequence for the C-terminal CUSI-I domain. The plasmid thus constructed is designated pBA17.

Then component E. coli K12 JM101 cells are transformed with the DNA of the constructed expression plasmid pBA17. For expressing the C-terminal CUSI-I domain, 250 ml LB-Amp medium are inoculated with the obtained transformants. Then incubation is carried out at 37° C. Cell growth is monitored by determining clouding at 578 nm. At an optical density of 0.97 IPTG is added in a final concentration of 0.5 mM in order to induce expression. An aliquod of 1 $A_{578}$ unit cells is taken at different times before and after induction of the expression (see Table II below), centrifuged for 3 minutes at 12,000 g and the cell sediment is stored at −20° C. The expression product has 59 amino acids with the following sequence:

Asp-Pro-Val-Asp-Thr-Pro-Asn-Pro-Thr-Arg-Arg-
Lys-Pro-Gly-Lys-Cys-Pro-Val-Thr-Tyr-Gly-Gln-
Cys-Leu-Met-Leu-Asn-Pro-Pro-Asn-Phe-Cys-
Glu-Met-Asp-Gly-Gln-Cys-Lys-Arg-Asp-Leu-
Lys-Cys-Cys-Met-Gly-Met-Cys-Gly-Lys-Ser-
Cys-Val-Ser-Pro-Val-Lys-Ala-OH.

Test for the Inhibitory Activity of the C-terminal CUSI-I Domain Expressed in E. coli The chymotrypsin inhibition test (39) is carried out as described in example 4. The increase in the inhibitory activity of the E. coli crude extract vis-a-vis chymotrypsin is monitored in dependence of time. In each case half of the E. coli lysate (100 μl) is tested for inhibitory activity. The results are listed in table II.

TABLE II

Determination of the inhibitory activity of the C-terminal CUSI-I domain expressed in E. coli

| Sample taken before induction (hours) | m IU/ml culture | chymotrypsin activity of 2 pMol enzyme (%) |
|---|---|---|
| 2 | 0,624 | 90 |
| 2.5 | 1.88 | 75 |
| 3 | 2.00 | 77 |

TABLE II-continued
Determination of the inhibitory activity of the C-terminal CUSI-I domain expressed in *E. coli*

| Sample taken after induction (hours) | m IU/ml culture | chymotrypsin activity of 2 pMol enzyme (%) |
|---|---|---|
| 1 | 4.83 | 67 |
| 2 | 6.57 | 67 |
| 3 | 7.24 | 67 |
| 4 | 9.56 | 64 |
| 5 | 8.00 | 67 |
| 6 | 10.66 | 60 |
| 21 | 16.96 | 37 |

In Table III the microorganisms deposited in accordance with the Budapest Treaty are listed.

TABLE III

| Microorganism | Depository | Deposition Number |
|---|---|---|
| *E. coli* K12 MC1061 | DSM | 3631 |
| *E. coli* K12 JM101 | ATCC | 33876 |
| *E. coli* K12 DH1 | ATCC | 33849 |
| *E. coli* K12 W6 | DSM | 3632 |
| pBR322 | ATCC | 31344 |
| pUC18 | DSM | 3424 |
| pUR290 | DSM | 3417 |
| pWH701 | DSM | 3633 |
| pRK248cIts | ATCC | 33766 |
| pRH31 | DSM | 3634 |
| pRH34 | DSM | 3635 |
| pSP6 | DSM | 3904 |
| pRH1810 | DSM | 3905 |

References

1. Bodmer et al., Schweiz. med. Wschr. 144, 1359–1363 (1984)
2. Lewis, D. A., Biochem. Pharmacol. 33, 1705–1714 (1984)
3. Schiessler, H. et al., Bayer Symp. V, Proteinase Inhibitors, (Fritz, H., Tschesche, H., Greene, L. J. Truscheit, E., Eds.), pp. 147–155, Springer Verlag, Berlin (1974)
4. Wallner, O. and Fritz, H., Hoppe-Seyler's Z. Physiol. Chem. 355, 709–711 (1974)
5. Fritz, H. et al. (1975) in: Proteases and Biological Control (Reich, E., Rifkin, D. B. and Shaw, E., Eds.), 737–766, Cold Spring Harbor Laboratory
6. Wallner, O. et al. in: Protides of the Biological Fluids (Peters, H., ed) 23, 177–182, Pergamon Press, Oxford (1975)
7. Chirgwin, J. M. et al., Biochemistry 18, 5294–5299 (1979)
8. Thayer, R. E., Anal. Biochem. 98, 60–63 (1979)
9. Wallace, R. B. et al., Nucl. Acids Res. 9, 879–894 (1981)
10. Clark, L. et al., Meth. Enzymol. 68, 436–442 (1979)
11. Gershoni, J. M. and Palade, G. E. Anal. Biochem. 131, 1–15 (1983)
12. Towbin, H. et al., Proc. Natl. Acad. Sci. USA 76, 4350–4354 (1979)
13. Gubler, U. and Hoffman, B. J. Gene 25, 263–269 (1983)
14. Volkaert, G. et al. in: Advanced Molecular Genetics, Springer Verlag, Berlin, 255–257 (1984)
15. Casadaban, M. J. and Cohen, S. N., J. Mol. Biol. 138, 179–207 (1980)
16. Messing, J. et al., Nucl. Acids Res. 9, 309–321 (1981)
17. Hanahan, D., J. Mol. Biol. 166, 557–580 (1983)
19. McDonnell, M. W. et al., J. Mol. Biol. 110, 119 (1977)
20. Bailey, J. M. and Davidson, N., Anal. Biochem. 70, 75–85 (1976)
21. Laemmli, U. K., Nature 227, 680–685 (1970)
22. Maxam, A. M. and Gilbert, W., Meth. Enzymol. 65, 499–580 (1980)
23. Bolivar, F. et al., Gene 2, 95–113 (1977)
24. Yanish-Perron, C. et al., Gene 33, 103–119 (1985)
25. Rüther, U. Müller-Hill, B. EMBO-J 2, 1791–1794 (1983)
26. C. Gatz, TH Darmstadt, Dissertation, 89–93 (1985)
27. Bernard, H. U. et al., Gene 5, 59–76 (1979)
28. Maniatis, T. et al.: Molecular cloning: A laboratory manual, Cold Spring Harbor Larboratory, Cold Spring Harbor, N.Y., 194 (1982); Bonner, T. I. et al., J. Mol. Biol., 81, 123 (1973)
29. Glisin, V. et al., Biochemistry 13, 2633 (1974)
30. Aviv, H. and Leder, P., Proc. Natl. Acad. Sci. USA 69, 1408 (1972)
31. Thomas, P. S., Proc. Natl. Acad. Sci. USA 77, 5201 (1980)
32. Suggs, S. V. et al., Developmental biology using purified genes (D. Brown, ed.), Academic Press, N.Y., 683 (1981)
33. Mandel, M. and Higa, A., J. Mol. Biol. 53, 159–162 (1970)
34. Hardies, S. C. et al., J. Biol. Chem. 254, 5527–5534 (1979)
35. Holmes, D. S. and Quigley, M. Anal. Biochem. 114, 193–197 (1981)
36. Caruthers, M. H., in Chemical and Enzymatic Gene Synthesis (H. G. Gassen, A. Lang eds.), 1st ed., Verlag Chemie, Weinheim (1982)
37. Ullmann, A., Gene 29, 27–31 (1984)
38. Fritz, H. et al.: Methoden der enzymatischen Analyse (H. U. Bergmeyer, ed.), 3rd ed., 1105, Verlag Chemie, Weinheim (1974)
39. DelMar, E. G. et al., Anal. Biochem. 99, 316–320 (1979)
40. Pelham, R. B. and Jackson, R. J., Eur. J. Biochem. 67, 247–256 (1976)
41. Klasen, E. C. and Kramps, J. A., Biochem. Biophys. Res. Comm. 128, 285–289 (1985)
42. Guarente, L. et al., Science 209, 1428–1430 (1980)
43. Miller, J. H. Experiments in Molecular Genetics, Cold Spring Harbor Laboratory, Cold Spring Harbor, N.Y., 433 (1972)
44. Ohlson, K. et al., Hoppe-Seyler's Z. Physiol. Chem. 357, 1241–1244 (1977)
45. Hochstrasser, K. et al., Hoppe-Seyler's Z. Physiol. Chem. 362, 1369–1375 (1981)
46. Smith, C. E. and Johnson, D. A. Biochem. J. 225, 463–472 (1985)
47. Schiessler, H. et al., Neutral Proteinases of Human Polymorphnuclear Leukocytes (Havemann, K. and Janoff. A., eds.), 195–207, Urban and Schwarzenberg, Baltimore, Munich (1978)
48. Fritz, H. in.: Protein Degradation in Health and Disease, Ciba Foundation Symposium 75, 351–379, publ. Excerpta Medica, Elsvier, North Holland (1980)
49. Bernard, H.-U., Methods Enzymol. 68, 482–492 (1979)

50. Machleidt, W., Modern Methods in Protein Chemistry (Tschesche, H., ed.), 267–302, Walter de Gruyter, Berlin, N.Y. (1983)

What is claimed is:

1. An acid resistant proteinase inhibitor HUSI-type I protein having the biological activity of the CUSI-type I protein and an amino acid sequence of the formula +18
Cys—Leu—Arg—Tyr—Lys—Lys—Pro—Glu—Gln—Ser—Asp—
Trp—Gln—Cys—Pro—Gly—Lys—Lys—Arg—Cys—Cys—Pro—
Asp—Thr—Cys—Gly—Ile—Lys—Cys—Leu—Asp—Pro—Val—
Asp—Thr—Pro—Asn—Pro—Thr—Arg—Arg—Lys—Pro—Gly—
Lys—Cys—Pro—Val—Thr—Gly—Gln—Cys—Leu—Met—Leu—
Asn—Pro—Pro—Asn—Phe—Cys—Glu—Met—Asp—Gly—Gln—
Cys—Lys—Arg—Asp—Leu—Lys—Cys—Cys—Met—Gly—Met—
+107
Cys—Gly—Lys—Ser—Cys—Val—Ser—Pro—Val—Lys—Ala.

2. The acid resistant proteinase inhibitor HUSI-type I protein having the biological activity of the CUSI-type I protein and an amino acid sequence of the formula +49
Asp—Pro—Val—Asp—Thr—Pro—Asn—Pro—Thr—Arg—Arg—
Lys—Pro—Gly—Lys—Cys—Pro—Val—Thr—Tyr—Gly—Gln—
Cys—Leu—Met—Leu—Asn—Pro—Pro—Asn—Phe—Cys—Glu—
Met—Asp—Gly—Gln—Cys—Lys—Arg—Asp—Leu—Lys—Cys—
Cys—Met—Gly—Met—Cys—Gly—Lys—Ser—Cys—Val—Ser—
+107
Pro—Val—Lys—Ala.

3. The acid resistant proteinase inhibitor HUSI-type I protein having the biological activity of the CUSI-type I protein and an amino acid sequence of the formula +50
Pro—Val—Asp—Thr—Pro—Asn—Pro—Thr—Arg—Arg—Lys—
Pro—Gly—Lys—Cys—Pro—Val—Thr—Tyr—Gly—Gln—Cys—
Leu—Met—Leu—Asn—Pro—Pro—Asn—Phe—Cys—Glu—Met—
Asp—Gly—Gln—Cys—Lys—Arg—Asp—Leu—Lys—Cys—Cys—
Met—Gly—Met—Cys—Gly—Lys—Ser—Cys—Val—Ser—Pro—
+107
Val—Lys—Ala.

4. A composition comprising an acid resistant proteinase inhibitor HUSI-type I protein according to any one of claims 1, 2 or 3 in a form essentially free from impurities which interfere with the activity of said protein as an anti-inflammatory agent, in an amount effective to treat chronic imflammatory disease or postoperative hemorrhages; and a pharmaceutically acceptable carrier, diluent or excipient therefor.

5. A method of treating a patient suffering from a chronic inflammatory disease or postoperative hemorrhages, which comprises administration to said patient of an amount effective to treat chronic inflammatory disease or postoperative hemorrhages of an acid-resistant proteinase inhibitor HUSI-type I protein according to any one of claims 1, 2 or 3.

6. The method of claim 5, which comprises inhalation of said acid resistant proteinase inhibitor HUSI-type I protein.

* * * * *